US011246671B2

(12) United States Patent
Itkowitz et al.

(10) Patent No.: US 11,246,671 B2
(45) Date of Patent: Feb. 15, 2022

(54) SYSTEMS AND METHODS FOR RECENTERING INPUT CONTROLS

(71) Applicant: INTUITIVE SURGICAL OPERATIONS, INC., Sunnyvale, CA (US)

(72) Inventors: Brandon D. Itkowitz, San Jose, CA (US); Michael L. Hanuschik, Mountain View, CA (US); Paul W. Mohr, Mountain View, CA (US); Arjang M. Hourtash, San Francisco, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 298 days.

(21) Appl. No.: 16/503,403

(22) Filed: Jul. 3, 2019

(65) Prior Publication Data
US 2019/0321117 A1    Oct. 24, 2019

Related U.S. Application Data

(63) Continuation of application No. 15/125,679, filed as application No. PCT/US2015/021105 on Mar. 17, 2015, now Pat. No. 10,398,521.
(Continued)

(51) Int. Cl.
*A61B 1/00* (2006.01)
*A61B 34/35* (2016.01)
(Continued)

(52) U.S. Cl.
CPC .......... *A61B 34/35* (2016.02); *A61B 1/00149* (2013.01); *A61B 1/3132* (2013.01);
(Continued)

(58) Field of Classification Search
CPC ......... A61B 34/35; A61B 34/25; A61B 35/30; A61B 35/37; A61B 35/70; A61B 35/74;
(Continued)

(56) References Cited

U.S. PATENT DOCUMENTS 5,390,288 A    2/1995    Toda et al.
5,817,084 A   10/1998    Jensen et al.
(Continued)

FOREIGN PATENT DOCUMENTS

EP           3119323 A1    1/2017
JP        2005261956 A    9/2005
(Continued)

OTHER PUBLICATIONS

Burgner J., et al., "A Bimanual Teleoperated System for Endonasal Skull Base Surgery," IEEE/RSJ International Conference on Intelligent Robots and Systems(IROS), Sep. 2011. pp. 2517-2523.
(Continued)

*Primary Examiner* — Timothy J Neal
*Assistant Examiner* — William B Chou
(74) *Attorney, Agent, or Firm* — Artegis Law Group, LLP

(57) ABSTRACT

Systems and methods of recentering an input control include a control unit configured to suspend teleoperated control of an end effector by the input control in response to a recentering request, determine a recentering move for the input control to provide positional and orientational harmony between the input control and the end effector, execute the recentering move, and reinstate teleoperated control of the end effector by the input control. In some embodiments, to determine the recentering move the control unit is configured to determine one or more first positions associated with the end effector, map the first positions to a view coordinate system, map the first positions from the view coordinate system to a console workspace coordinate sys-
(Continued)

tem, and determine one or more second positions for one or more control points on the input control, the control points corresponding to the mapped first positions in the console workspace coordinate system.

20 Claims, 10 Drawing Sheets

Related U.S. Application Data

(60) Provisional application No. 61/954,191, filed on Mar. 17, 2014.

(51) Int. Cl.
| | | |
|---|---|---|
| A61B 34/30 | (2016.01) | |
| A61B 34/37 | (2016.01) | |
| A61B 90/00 | (2016.01) | |
| A61B 34/00 | (2016.01) | |
| A61B 1/313 | (2006.01) | |
| A61B 34/20 | (2016.01) | |

(52) U.S. Cl.
CPC .............. *A61B 34/25* (2016.02); *A61B 34/30* (2016.02); *A61B 34/37* (2016.02); *A61B 34/74* (2016.02); *A61B 90/37* (2016.02); *A61B 2034/2057* (2016.02); *A61B 2034/301* (2016.02)

(58) Field of Classification Search
CPC .... A61B 90/37; A61B 1/00149; A61B 1/3132
See application file for complete search history.

(56) References Cited

U.S. PATENT DOCUMENTS

| | | | |
|---|---|---|---|
| 6,468,265 | B1 | 10/2002 | Evans et al. |
| 8,004,229 | B2 | 8/2011 | Nowlin et al. |
| 8,189,738 | B2 | 5/2012 | Dussault et al. |
| 8,332,072 | B1 | 12/2012 | Schaible et al. |
| 8,541,970 | B2 | 9/2013 | Nowlin et al. |
| 8,620,473 | B2 | 12/2013 | Diolaiti et al. |
| 8,624,537 | B2 | 1/2014 | Nowlin et al. |
| 8,749,189 | B2 | 6/2014 | Nowlin et al. |
| 8,749,190 | B2 | 6/2014 | Nowlin et al. |
| 8,786,241 | B2 | 7/2014 | Nowlin et al. |
| 8,816,628 | B2 | 8/2014 | Nowlin et al. |
| 8,823,308 | B2 | 9/2014 | Nowlin et al. |
| 9,066,737 | B2 | 6/2015 | Bärwinkel et al. |
| 9,084,623 | B2 | 7/2015 | Gomez et al. |
| 9,138,129 | B2 | 9/2015 | Diolaiti |
| 9,333,042 | B2 | 5/2016 | Diolaiti et al. |
| 9,469,034 | B2 | 10/2016 | Diolaiti et al. |
| 9,516,996 | B2 * | 12/2016 | Diolaiti ............... A61B 1/00039 |
| 9,717,563 | B2 * | 8/2017 | Tognaccini ............. A61B 1/04 |
| 9,774,827 | B2 | 9/2017 | Tanaka et al. |
| 10,258,425 | B2 * | 4/2019 | Mustufa ................. A61B 90/36 |
| 10,398,521 | B2 | 9/2019 | Itkowitz et al. |
| 2002/0093484 | A1 * | 7/2002 | Skala ...................... A61B 1/041 345/163 |
| 2002/0128552 | A1 | 9/2002 | Nowlin et al. |
| 2004/0015053 | A1 | 1/2004 | Bieger et al. |
| 2006/0241414 | A1 | 10/2006 | Nowlin et al. |
| 2007/0156126 | A1 | 7/2007 | Flaherty |
| 2009/0192524 | A1 | 7/2009 | Itkowitz et al. |
| 2009/0245600 | A1 | 10/2009 | Hoffman et al. |
| 2010/0161129 | A1 | 6/2010 | Costa et al. |
| 2010/0228265 | A1 | 9/2010 | Prisco |
| 2010/0331856 | A1 | 12/2010 | Carlson et al. |
| 2011/0230896 | A1 | 9/2011 | Wallace et al. |
| 2012/0320186 | A1 | 12/2012 | Urban et al. |
| 2013/0060278 | A1 | 3/2013 | Bozung et al. |
| 2013/0103197 | A1 | 4/2013 | Mohr et al. |
| 2013/0190776 | A1 | 7/2013 | Zhang et al. |
| 2013/0211588 | A1 | 8/2013 | Diolaiti |
| 2013/0304084 | A1 | 11/2013 | Beira et al. |
| 2013/0331644 | A1 | 12/2013 | Pandya et al. |
| 2014/0039521 | A1 | 2/2014 | Mohr et al. |
| 2014/0039681 | A1 | 2/2014 | Bowling et al. |
| 2014/0163359 | A1 | 6/2014 | Sholev et al. |
| 2014/0194896 | A1 * | 7/2014 | Frimer ............... A61B 1/00009 606/130 |
| 2014/0221738 | A1 * | 8/2014 | Sholev ............... A61B 1/00149 600/102 |
| 2014/0228632 | A1 | 8/2014 | Sholev et al. |
| 2014/0277747 | A1 | 9/2014 | Walker et al. |
| 2014/0323803 | A1 | 10/2014 | Hoffman et al. |
| 2015/0032126 | A1 | 1/2015 | Nowlin et al. |
| 2015/0051733 | A1 | 2/2015 | Nowlin et al. |
| 2016/0015473 | A1 * | 1/2016 | Frimer ............... A61B 1/00149 606/130 |
| 2016/0038011 | A1 | 2/2016 | Diolaiti et al. |
| 2016/0354166 | A1 | 12/2016 | Popovic et al. |
| 2017/0000574 | A1 | 1/2017 | Itkowitz et al. |
| 2017/0202629 | A1 | 7/2017 | Maillet et al. |
| 2017/0212723 | A1 * | 7/2017 | Atarot .................... G06F 3/167 |
| 2021/0030502 | A1 | 2/2021 | Verner |

FOREIGN PATENT DOCUMENTS

| | | |
|---|---|---|
| KR | 20130092615 A | 8/2013 |
| KR | 20130121590 A | 11/2013 |
| WO | WO-2006124390 A2 | 11/2006 |
| WO | WO-2010117685 A2 | 10/2010 |
| WO | WO-2010151438 A1 | 12/2010 |
| WO | WO-2011060139 A2 | 5/2011 |
| WO | WO-2013027200 A2 | 2/2013 |
| WO | WO-2013027201 A2 | 2/2013 |
| WO | WO-2013027202 A2 | 2/2013 |
| WO | WO-2013122889 A1 | 8/2013 |
| WO | WO-2015121765 A1 | 8/2015 |
| WO | WO-2015142953 A1 | 9/2015 |

OTHER PUBLICATIONS

Extended European Search Report for Application No. EP19191254.2, dated Oct. 24, 2019, 6 pages.
International Search Report and Written Opinion for Application No. PCT/US15/21105, dated Jun. 5, 2015, 11 pages.
Bajdt et al., "Robotics" In: "Robotics", Jan. 15, 2010 (Jan. 15, 2010), Springer Netherlands, Dordrecht, XP055384691, ISBN: 978-90-48-13776-3, 1 page.
Extended European Search Report for Application No. 15764617.5, dated Jul. 5, 2017, 9 pages.
King, B. W., et al., "Towards an Autonomous Robot for Camera Control during Laparoscopic Surgery," Journal of Laparoendoscopic & Advanced Surgical Techniques, vol. 23 (12), 2013, pp. 1027-1030.
Mudunuri, A. V., "Autonomous camera control system for surgical robots," Wayne State University Thesis, DigitalCommons, 2010, 87 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2018/056874, dated May 7, 2020, 8 pages.
International Search Report and Written Opinion for Application No. PCT/US2018/056874, dated Feb. 1, 2019, 10 pages.
Extended European Search Report for Application No. EP18871669.0 dated Nov. 12, 2020, 8 pages.
Extended European Search Report for Application No. EP21170697.3 dated Aug. 20, 2021, 8 pages.

* cited by examiner

SYSTEMS AND METHODS FOR RECENTERING INPUT CONTROLS

RELATED APPLICATIONS

The present application is a continuation of U.S. patent application Ser. No. 15/125,679, filed Sep. 13, 2016, which is the U.S. national phase of International Application No. PCT/US2015/021105, filed Mar. 17, 2015, which designated the U.S. and further claims priority to U.S. Provisional Patent Application No. 61/954,191 entitled "System and Method for Recentering Imaging Devices and Input Controls" filed Mar. 17, 2014. Each of which is hereby incorporated reference in its entirety.

TECHNICAL FIELD

The present disclosure relates generally to teleoperation of devices with articulated arms and more particularly to recentering imaging devices and input controls.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. It is also common to operate the electronic devices via teleoperation using one or more input controls on an operator workstation to control the motion and/or operation of the articulated arms and/or the end effectors. When the electronic device is operated remotely from the operator workstation and/or the end effectors are being used in an area not directly visible to the operator, such as during computer-assisted surgery when the end effectors are hidden by patient anatomy, the electronic device may include an imaging device that captures a region of interest and displays it to the operator using a display system. As the operator controls the articulated arms and/or the end effectors, the operator generally tries to keep the end effectors in sight of the imaging device so that the operation of the end effectors may be observed on the display system. In addition, the positions and orientations of the input controls are typically matched to the end effectors so that as the input controls are moved, the end effectors "follow" those moves.

As the imaging device and/or the end effectors are moved, it is possible that the operator may lose sight of one or more of the end effectors and/or lose track of the spatial relationships between the imaging device and the end effectors. This may further be complicated when the operator of the electronic device switches control to additional articulated arms and/or end effectors that may be parked in other areas around the region of interest and/or when the end effectors are partially or totally occluded by other objects in the region of interest. To reacquire visualization of the end effectors (i.e., to place the end effectors within the view volume of the imaging device), the operator may have to perform a series of recentering movements with the imaging device to find a suitable pose (position and orientation) of the imaging device that includes the end effectors. This series of movements may become cumbersome, prolonged and/or impractical.

In addition, as the imaging device is moved and/or the input controls are switched to the additional articulated arms and/or end effectors, the spatial orientations between the imaging device and the end effectors may be changed. This may result in disharmony between the positions and/or orientations of the end effectors as displayed by the display system and the corresponding positions and/or orientations of the input controls for those end effectors. In some cases this may be corrected by the operator by activating a clutch for the input controls and then repositioning and/or reorienting the input controls to match the end effector positions and/or orientations as shown on the display system. As with the movements of the imaging device, these repositioning and/or reorienting operations may also become cumbersome, prolonged and/or impractical.

Accordingly, improved methods and systems for visually reacquiring end effectors and/or repositioning and/or reorienting input controls to match the end effectors are desirable.

SUMMARY

Consistent with some embodiments, a computer-assisted medical device includes one or more end effectors, an imaging device, one or more input controls for teleoperating the one or more end effectors, and a control unit including one or more processors coupled to the end effectors, the imaging device, and the input controls. The control unit suspends teleoperated control of the end effectors by the input controls in response to a recentering request, determines a view recentering move for the imaging device so that the end effectors are contained within a view space of the imaging device, determines one or more input control recentering moves to provide positional and orientational harmony between each of the input controls and a corresponding one of the end effectors, executes the view and input control recentering moves, and reinstates teleoperated control of the end effectors by the input controls.

Consistent with some embodiments, a method of controlling motion in a medical device includes suspending teleoperated control of one or more end effectors of the medical device by one or more input controls of the medical device in response to a recentering request, determining a view recentering move for the imaging device so that the end effectors are contained within a view space of an imaging device of the medical device, determining one or more input control recentering moves to provide positional and orientational harmony between each of the input controls and a corresponding one of the end effectors, executing the view and input control recentering moves, and reinstating teleoperated control of the end effectors by the input controls.

Consistent with some embodiments, a method of controlling motion in a medical device includes suspending teleoperated control of one or more end effectors of the medical device by one or more input controls of the medical device in response to a recentering request, determining a view recentering move for the imaging device so that the end effectors are contained within a view space of an imaging device of the medical device, executing the view recentering move, and reinstating teleoperated control of the end effectors by the input controls.

Consistent with some embodiments, a method of determining a preferred working distance of an imaging device of a medical device includes detecting a start of a repositioning movement for an imaging device of the medical device, detecting an end of the repositioning movement, determining a current working distance based on first distances between the imaging device and one or more targets associated with one or more end effectors of the medical device that are within a view volume of the imaging device at the end of the repositioning movement, the first distances being measured in a direction of view of the imaging device, and aggregating the current working distance with previously obtained current working distances to determine the preferred working distance.

Consistent with some embodiments, a method of controlling motion in a medical device includes suspending teleoperated control of one or more end effectors of the medical device by one or more input controls of the medical device in response to a recentering request, determining one or more input control recentering moves to provide positional and orientational harmony between each of the input controls and a corresponding one of the end effectors, executing the input control recentering moves, and reinstating teleoperated control of the end effectors by the input controls.

Consistent with some embodiments, a method of determining an ergonomic center for an operator workstation of a medical device includes detecting a start of a repositioning movement for one or more input controls of the medical device, detecting an end of the repositioning movement, determining positions of one or more control points associated with the input controls at the end of the repositioning movement, aggregating the positions to determine an input control center point, and aggregating the input control center point with previously obtained input control center points to determine the ergonomic center.

Consistent with some embodiments, a non-transitory machine-readable medium includes a plurality of machine-readable instructions. When the machine-readable instructions are executed by one or more processors associated with a medical device, they cause the one or more processors to perform a method. The method includes suspending teleoperated control of one or more end effectors of the medical device by one or more input controls of the medical device in response to a recentering request, determining a view recentering move for the imaging device so that the end effectors are contained within a view space of an imaging device of the medical device, determining one or more input control recentering moves to provide positional and orientational harmony between each of the input controls and a corresponding one of the end effectors, executing the view and input control recentering moves, and reinstating teleoperated control of the end effectors by the input controls.

Consistent with some embodiments, a method of controlling motion of an imaging device coupled to a medical device includes detecting activation of an imaging device motion mode and determining whether one or more motion input controls are being used. When the one or more motion input controls are being used, controlling a pose of the imaging device based on the one or more motion input controls. When the one or more motion input controls are not being used for a timeout period, recentering the imaging device. Recentering the imaging device includes determining a view recentering move for the imaging device so that one or more end effectors of the medical device are contained within a view space of the imaging device and executing the view recentering move.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
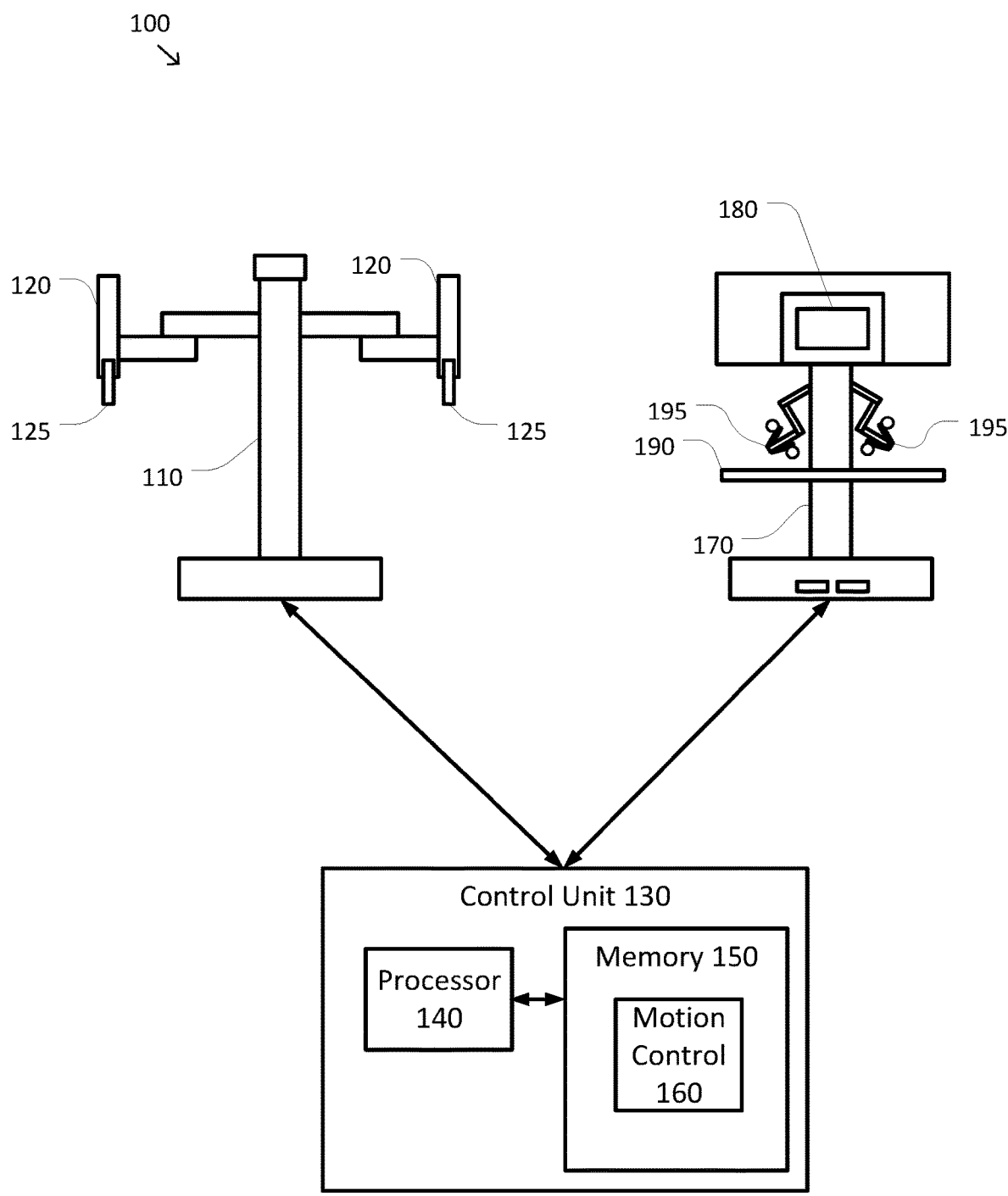
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 may support one or more end effectors 125. In some examples, device 110 may be consistent with a computer-assisted surgical device. The one or more end effectors 125 may include surgical instruments, imaging devices, and/or the like. In some examples, the surgical instruments may include clamps, grippers, retractors, cautery tools, suction tools, suturing devices, and/or the like. In some examples, the imaging devices may include endoscopes, cameras, stereoscopic devices, and/or the like.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, and/or planning and/or assisting in the planning of motion for device 110, articulated arms 120, and/or the end effectors 125 of device 110. And although motion control application 160 is depicted as a software application, motion control application 160 may be implemented using hardware, software, and/or a combination of hardware and software.

Control unit 130 may further be coupled to an operator workstation 170 via the interface. Operator workstation 170 may be used by an operator, such as a surgeon, to control the movement and/or operation of the articulated arms 120 and the end effectors 125. To support operation of the articulated arms 120, operator workstation 170 includes a display system 180 for displaying images of at least portions of one or more of the articulated arms 120 and/or end effectors 125. For example, display system 180 may be used when it is impractical and/or impossible for the operator to see the articulated arms 120 and/or the end effectors 125 as they are being used. Operator workstation 170 may further include a console workspace with one or more input or master controls 195 that may be used for operating the device 110, the articulated arms 120, and/or the end effectors 125. Each of the input controls 195 may be coupled to the distal end of their own articulated arms so that movements of the input controls 195 may be detected by the operator workstation 170 and communicated to control unit 130. To provide improved ergonomics, the console workspace may also include one or more rests, such as an arm rest 190 on which operators may rest their arms while manipulating the input controls 195. In some examples, the display system 180 and the input controls 195 may be used by the operator to teleoperate the articulated arms 120 and/or the end effectors 125. In some embodiments, device 110, operator workstation 170, and control unit 130 may correspond to a da Vinci® Surgical System commercialized by Intuitive Surgical, Inc. of Sunnyvale, Calif.

In some embodiments, other configurations and/or architectures may be used with computer-assisted system 100. In some examples, control unit 130 may be included as part of operator workstation 170 and/or device 110. In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms 120 and/or end effectors 125.

Figure 2:
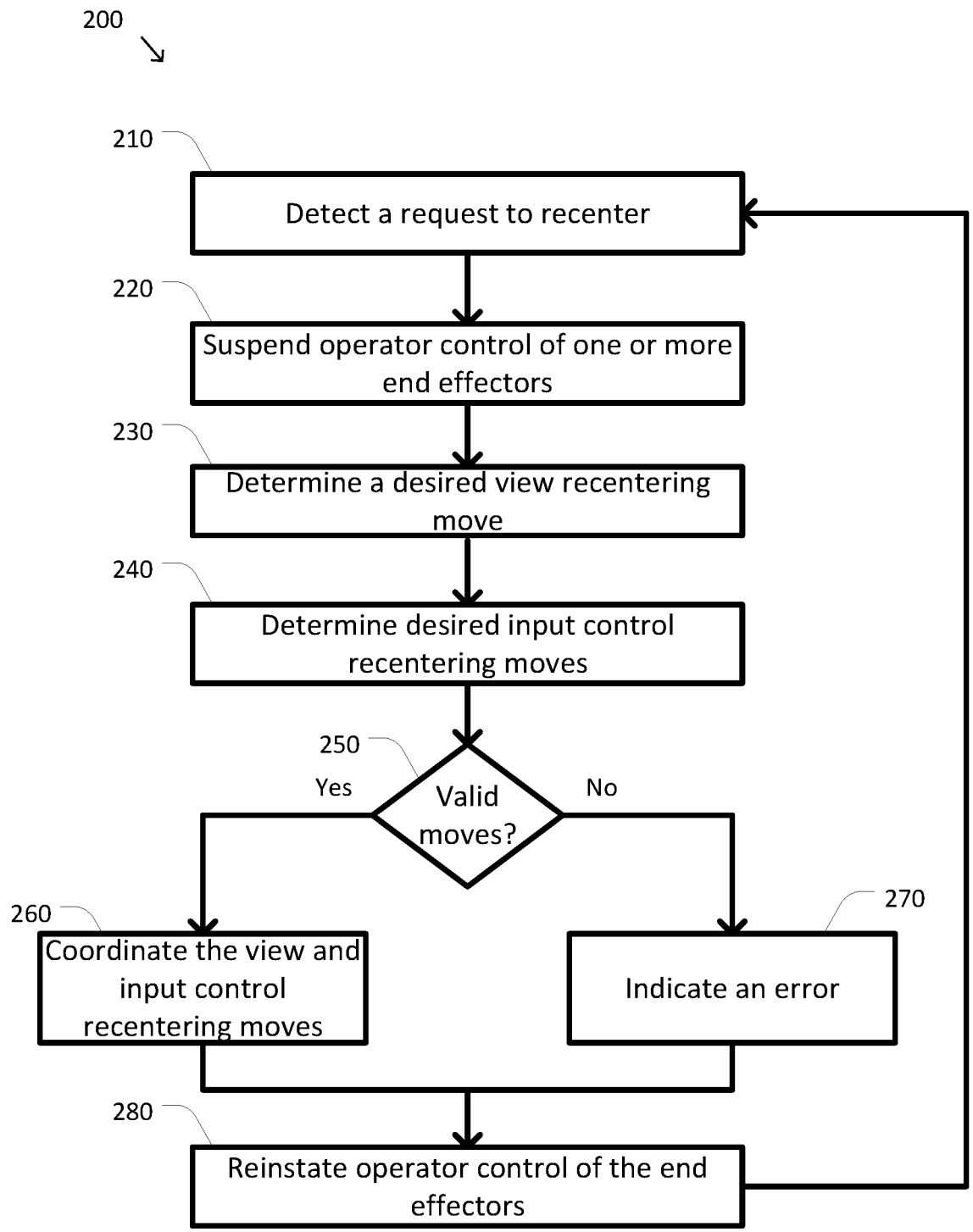
FIG. 2 is a simplified diagram of a method of recentering end effectors and input controls according to some embodiments.

FIG. 2 is a simplified diagram of a method 200 of recentering end effectors and input controls according to some embodiments. One or more of the processes 210-280 of method 200 may be implemented, at least in part, in the form of executable code stored on non-transient, tangible, machine readable media that when run by one or more processors (e.g., the processor 140 in control unit 130) may cause the one or more processors to perform one or more of the processes 210-280. In some embodiments, method 200 may be performed by an application, such as motion control application 160. In some embodiments, method 200 may be used to recenter one or more of the end effectors 125 in an image captured by an imaging device and displayed on display system 180 and/or recenter one or more of the input controls 195 in the console workspace so that the positions and/or orientations of the input controls 195 corresponds with the positions and/or orientations of the end effectors 125 displayed in the image.

At a process 210, a request to recenter is detected. In some examples, an operator of an electronic device may manually trigger the request to recenter using one or more input controls such as a switch, a pedal, a level, voice recognition, and/or the like. In some example, the request may be issued as a momentary input which triggers recentering and/or as a continuous input which activates the recentering until its completion and/or the input is withdrawn. In some examples, the request to recenter may be automated in response to a change in system state. In some examples, the change in system state may include a change in association between the input controls and the teleoperated end effectors. In some examples, the change in system state may include a change in association between the input controls and the teleoperated end effectors in which one or more end effectors is detected to be outside the field of view of the imaging device. In some examples, the change in system state may include a change in the mode of the imaging device that results in one or more end effectors being outside the field of view of the imaging device (e.g. change of digital zoom, change of distal viewing angle, and/or the like). In some examples, the request to recenter may also include a designation of the articulated arms and end effectors that are to be recentered upon. In some examples, detection of the request to recenter may be acknowledged by suitable feedback to an operator, such as a unique sound, a message on a console, an indicator, and/or the like.

At a process 220, operator control of one or more end effectors is suspended. Before recentering may begin, the ability of the operator to control and/or teleoperate one or more of the end effectors of the electronic device is suspended. Suspension of control by the operator permits the recentering operations to continue without interference from motions commanded by the operator.

At a process 230, a desired view recentering move is determined. Using, for example, sensed joint positions in the articulated arms and the end effectors coupled to the articulated arms and one or more kinematic models of the articulated arms and the end effectors, a view recentering move is determined. In some examples, this may include determining poses (e.g., positions and/or orientations) of one or more end effectors of interest associated with the electronic device being controlled. In some examples, each of the determined poses may be mapped to a common coordinate system, such as a world coordinate system and/or a view coordinate system. Using the geometries of the poses and knowledge of a preferred working distance for the imaging device, a desired pose for the imaging system is determined which places the end effectors within the view space of the imaging device. The pose and one or more kinematic models of the imaging device may then be used to determine the desired view recentering move for the imaging device.

At a process 240, desired input control recentering moves are determined. The poses for the end effectors determined during process 230 may be mapped to a coordinate system for a console workspace in which input controls corresponding to the end effectors are located. The poses may be mapped using knowledge of a preferred ergonomic center of the console workspace and scale factors between distances in the workspace used by the end effectors and distances in the console workspace containing the input controls. The mapped poses and one or more kinematic models for the input controls may then be used to determine corresponding input control recentering moves for the input controls. In some embodiments, two input control recentering moves are determined, one corresponding to a left input control associated with a first one of the end effectors and another corresponding to a right input control associated with a second one of the end effectors. In some embodiments, other numbers of input controls may also have corresponding recentering moves determined.

At a process 250, it is determined whether the view recentering move and/or the input control recentering moves are valid. Using the kinematic models of the imaging device and the desired recentering move for the imaging device determined during process 230, it is determined whether the desired recentering move for the image device is valid. In some examples, this validity determination may include reviewing one or more constraints on movement of the imaging device, location of other articulated arms, other end effectors, and/or devices in the workspace of the electronic device, and/or ability of the imaging device to obtain a suitable image of the end effectors. Using the kinematic models of the input controls and the desired recentering moves for the input controls determined during process 240, it is determined whether the desired recentering moves for the input controls are valid. In some examples, this validity determination may include reviewing one or more constraints on movement of the input controls, location of portions of the operator workstation in the console workspace, and/or ergonomic considerations for the operator of the input controls. When the recentering moves are determined to be valid, the recentering moves are performed using a process 260. When any of the recentering moves are determined to be invalid, an error is indicated using a process 270.

At the process 260, the view and input control recentering moves are coordinated. One or more movement commands are sent to one or more actuators of the articulated arm coupled to the imaging device to command and/or direct the imaging device to execute the view recentering move. One or more movement commands are also sent to one or more actuators of the articulated arms coupled to the input controls to command and/or direct the input controls to execute the input control recentering moves. The movement commands for the imaging device and input controls are typically coordinated. In some examples, the coordination may permit concurrent recentering of both the imaging device and the input controls. In some examples, the coordination may be performed so that at least some positional and/or orientational harmony is being maintained between the end effectors within the view space of the imaging device and the poses of the input controls during the recentering moves. In some examples, process 260 may also include providing audio and/or visual feedback to the operator indicating that the recentering operations are taking place. In some examples, the audio feedback may include a unique sound, a spoken phrase, and/or the like. Upon completion of the recentering moves, operator control is resumed using a process 280.

At the process 270, an error is indicated. When the determined recentering moves are determined to be invalid, the operator is notified. In some examples, the notification may include any suitable audio and/or visual feedback. In some examples, the audio feedback may include playing of a unique sound. After the error is indicated, operator control is resumed using the process 280.

At the process 280, operator control of the end effectors is reinstated. Whether recentering moves are performed using process 260 or an error is indicated using process 270, control of the end effectors using the input controls is returned to the operator. When an error is indicated, recentering of the imaging device and/or the input controls may become the responsibility of the operator. After a period of control of the end effectors and/or the imaging device by the operator, another recentering operation may be detected using process 210.

As discussed above and further emphasized here, FIG. 2 is merely an example which should not unduly limit the scope of the claims. One of ordinary skill in the art would recognize many variations, alternatives, and modifications. According to some embodiments, additional conditions may result in premature termination of method 200 such as by returning operator control being using process 280 and/or by suspension of device operation. In some examples, the additional conditions may include manual intervention or override from an operator using one or more controls on the operator workstation or the articulated arms, detection of operator disengagement with the operator workstation using one or more safety interlocks, position tracking errors in the articulated arms and/or input controls, system faults, and/or the like.

Figure 3A:
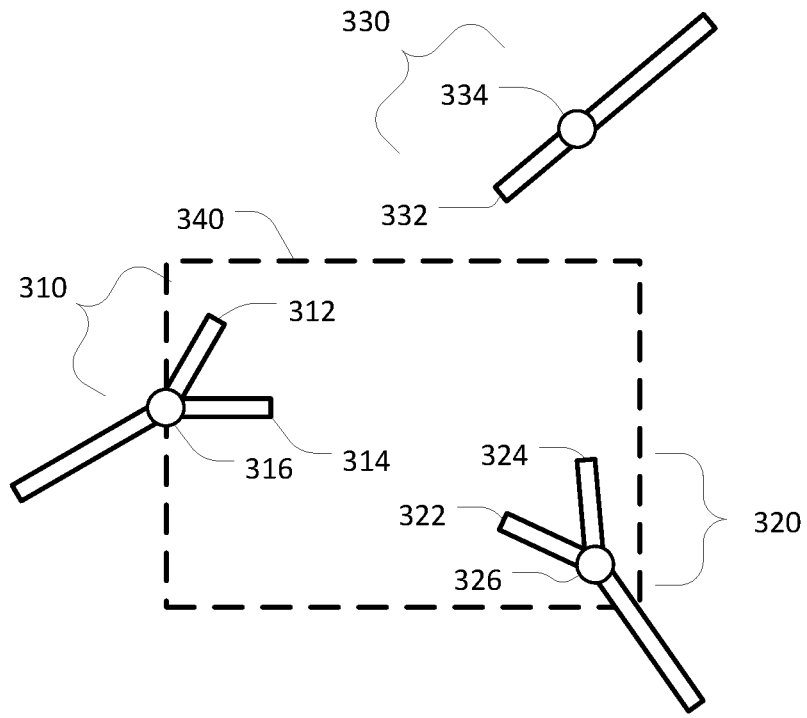
FIGS. 3A and 3B are simplified diagrams of an imaging view from before and after a view recentering operation according to some embodiments.
Figure 3B:
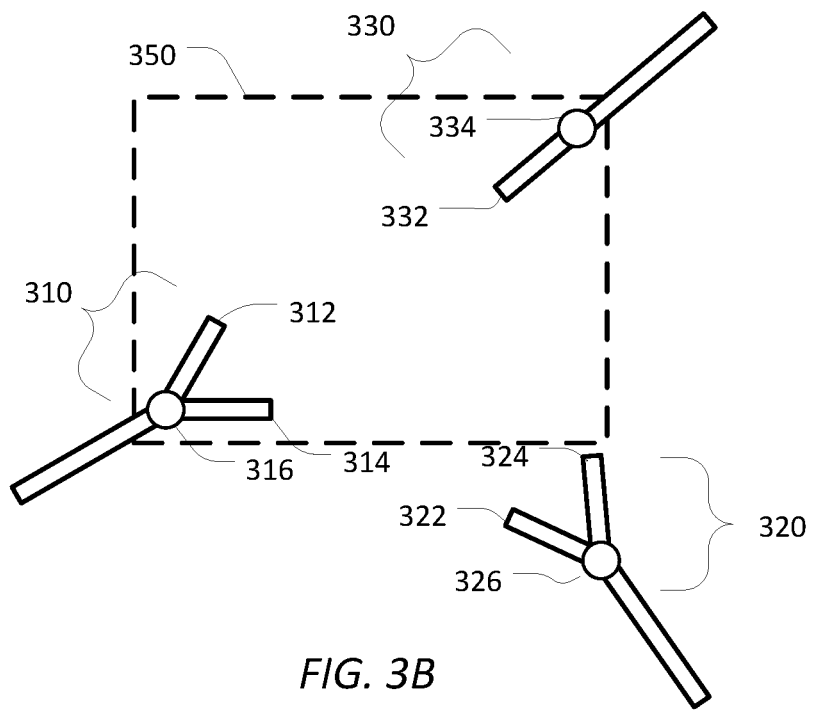

FIGS. 3A and 3B are simplified diagrams of an imaging view from before and after a view recentering operation according to some embodiments. As shown in FIG. 3A a workspace is shown including three articulated arms prior to the performance of a view recentering operation. A first articulated arm ends with a gripper-type end effector 310. The gripper-type end effector 310 includes two gripping fingers 312 and 314 and a pivot joint 316. A second articulated arm also ends with a gripper-type end effector 320 including two gripping fingers 322 and 334 and a pivot joint 326. A third articulated arm includes a single-finger end effector 330 including an end point 332 and a reference point 334. In some examples, reference point 334 may correspond to a rotational joint. In some examples, the single-finger end effector 330 may be representative of a cautery tool, a suction tool, and/or the like. In some examples, the articulated arms may be representative examples of the articulated arms 120 and the gripper-type and/or single-finger end effectors 310, 320, and/or 330 may be representative examples of the end effectors 125.

Also depicted in FIG. 3A is a view space 340. In some examples, view space 340 may correspond to an image captured by an imaging device. As shown, view space 340 contains the gripper-type end effector 320, a portion of the gripper-type end effector 310, and none of the single-finger end effector 330. In some examples, FIG. 3A may correspond to an image taken while an operator is controlling end effectors 310 and/or 320.

In some examples, when the operator desires to switch to controlling end effectors 310 and 330 rather than end effectors 310 and 320 this may create problems. For example, because end effector 330 is not within view space 340, end effector 330 is not visible in images of view space 340 and the operator may not remember where end effector 330 is located. In some examples, the operator may manually recenter the view space 340 to place both end effectors 310 and 330 within view space 340. In some examples, the operator may trigger automated recentering using a method like method 200 and designate end effectors 310 and 330 as the end effectors about which recentering is to take place.

FIG. 3B shows a view space 350 of end effectors 310 and 330 after recentering. Using a view recentering move, an imaging device used to capture images of the end effectors 310 and 330 is repositioned and/or reoriented to a pose that contains the end effectors 310 and 330. The recentering move changes the view space 340 from prior to the view recentering move to the view space 350 after the view recentering move takes place. This view recentering move results in the view space 350 containing the gripping fingers 312 and 314, the pivot joint 316, the end point 332, and the reference point 334. The view space 350 is also centered about the gripping fingers 312 and 314, the pivot joint 316, the end point 332, and the reference point 334.

Figure 4A:
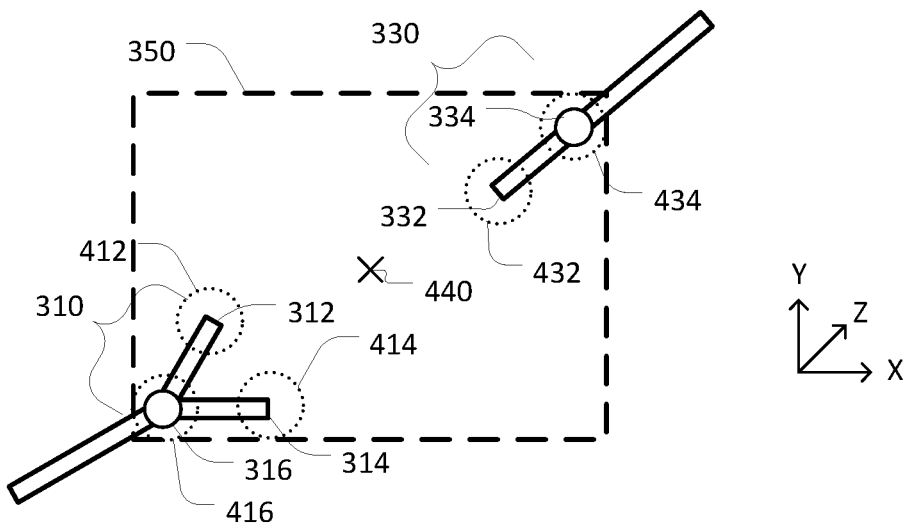
FIGS. 4A and 4B are simplified diagrams of an imaging view and a side view, respectively, after a view recentering operation according to some embodiments.
Figure 4B:
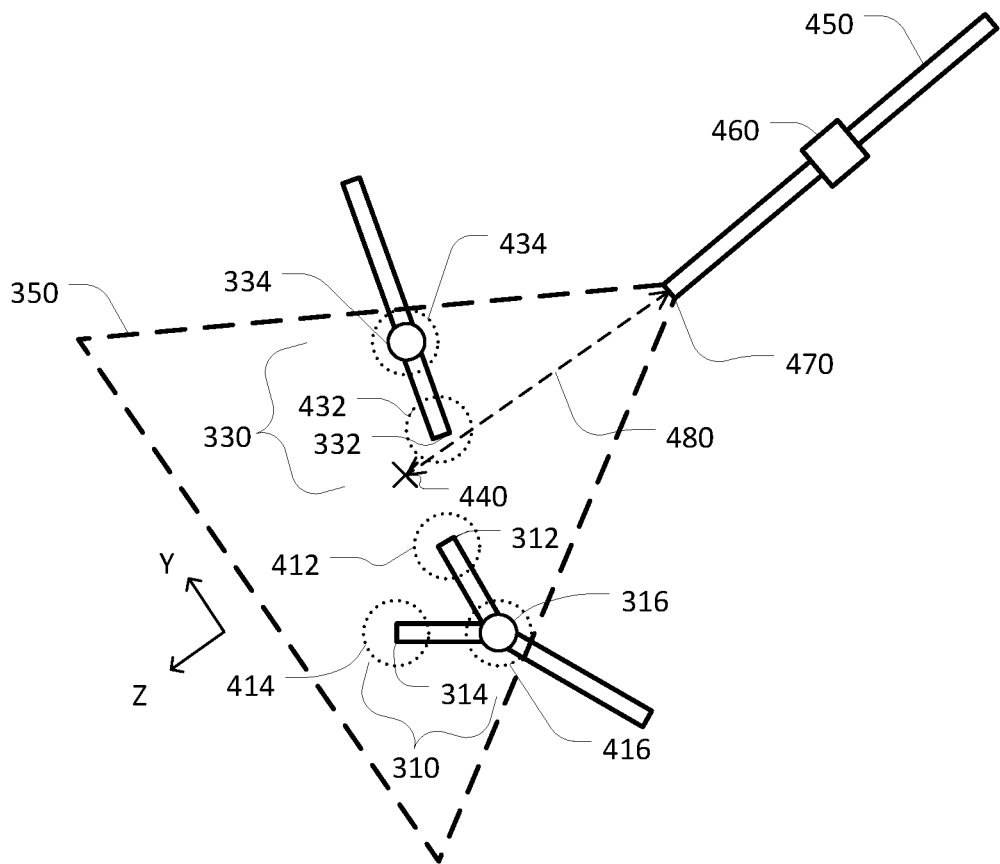

FIGS. 4A and 4B are simplified diagrams of an imaging view and a side view, respectively, after a view recentering operation according to some embodiments. FIGS. 4A and 4B show the use of targets on the end effectors 310 and 330 to center the view space 350 on end effectors 310 and 330. FIG. 4A shows this from images that may be captured by the imaging device using view space 350. In some examples, when a view coordinate system is used, the view space 350 may include an x-axis from left to right in view space 350, a y-axis in the view up direction, and a z-axis in the direction of view.

To help recenter the end effectors 310 and 330 in view space 350, one or more targets on each of the end effectors 310 and/or 330 are selected. In some embodiments, each of the targets may be associated with the tips of each of the fingers of the end effectors 310 and/or 330 as well as any of the joints and/or reference points that are of interest as is shown in FIG. 4A. In some embodiments, other criteria may be used to select the targets, such as associating targets on just the tips of the fingers and/or at other positions on the end effectors 310 and/or 330 and/or the associated articulated arms. As shown in FIG. 4A, three targets are used on the gripper-type end effector 310 and two targets are used on the single-finger end effector 330. The three targets on the gripper-type end effector 310 include targets 412 and 414 centered on the tips of the gripping FIGS. 312 and 314, respectively, and a targeting point 416 centered on the pivot joint 316. The two targets on the single-finger end effector 330 include a targeting point 432 centered on the end point 332 and a targeting point 434 centered on the reference point 334.

In some examples, each of the targets 412-416 and/or 432-434 may be modeled as virtual bounding spheres with centers at corresponding tips of the fingers and/or at or near the centers of the corresponding joints and/or the reference points. In some examples, the radius of each of the virtual spheres is large enough to capture at least the volume of the corresponding portion of the end effector associated with the respective targeting point. In some examples, the radius may be two to three times larger than the volume of the corresponding portion of the end effector so that view space 350 may capture the corresponding end effector as well as a margin of space about the corresponding end effector. This helps prevent having the end effectors placed just on the edges of view space 350. In some examples, the radius may be sized to account for kinematic uncertainty in the position of the target points.

In some examples, a centroid 440 of the center points of each of the targets 412-416 and/or 432-434 may be computed. Centroid 440 may then be used as a center point of view space 350. A working distance between centroid 440 and the imaging device may then be adjusted so that view space 350 includes each of the targets 412-416 and/or 432-434.

FIG. 4B shows a corresponding side view of view space 350. The side view of FIG. 4B shows that view space 350 is a viewing frustum that widens as it moves away from an imaging device 450. In some examples, an angular width of the frustum may be determined from optical properties of imaging device 450. In some examples, imaging device 450 may be an endoscope that is inserted into a patient through a cannula 460. In some examples, imaging device 450 may be stereoscopic. In some examples, the cannula 460 may be positioned near a remote center for imaging device 450 so that roll, pitch, and yaw rotations of imaging device 450 are centered about the remote center. As FIG. 4B further shows, imaging device 450 is oriented with centroid 440 along the direction of view in the z-direction of the view coordinate system. Centroid 440 may also be located at an average depth in the z-direction of each of the targets 412-416 and/or 332-334. Centroid 440 is also located at a working distance 480 from a tip 470 of imaging device 450.

In some embodiments, working distance 480 may be selected based on one or more criteria. The process begins by determining centroid 440 and using the direction from a reference point on the imaging device to centroid 440 as the viewing or z-axis direction. In some examples, the reference point may correspond to cannula 460 when the imaging device is straight between cannula 460 and tip 470. In some examples, one or more kinematic models of the imaging device may be used to determine the location of the reference point relative to the cannula 460. In some examples, the reference point may be associated with tip 470. A maximum x-axis and/or y-axis extent for each of the targets 412-416 and/or 432-434 are then used to determine respective minimum viewing distances for each of the targets 412-416 and/or 432-434 so that the targets 412-416 and/or 432-434 are within the frustum of view space 350. The largest minimum viewing distance may then be chosen as working distance 480 so as to ensure that the volumes associated with each of the targets 412-416 and/or 432-434 are contained within view space 350. In some examples, the working distance 480 may be increased to a preferred working distance for imaging device 450 when one is specified and it is larger than the largest minimum viewing distance. In some examples, working distance 480 may also be constrained to be within minimum and maximum focal distances for imaging device 450.

Once the viewing direction/view coordinate system z-axis and working distance 480 are determined, the view recentering move for imaging device 450 may be determined. The view recentering move may include adjusting the pitch and yaw of imaging device 450 to align with the viewing direction and adjusting the amount of insertion and/or retraction of tip 470 relative to cannula 460 based on working distance 480. In some examples, the view recentering move may be analyzed to determine whether it is valid. In some examples, this may include determining whether the articulated arm to which imaging device 450 is attached may execute the view recentering move. In some examples, the articulated arm may not be able to execute the view recentering move due to joint limitations, maximum movement limitations placed on view recentering moves, and/or collision avoidance with other articulated arms (e.g., articulated arms 310, 320, and/or 330), patient anatomy, and/or other objects in the work space. In some examples, the maximum movement limitations may include pitch and yaw angular limits that limit pitch and yaw motions below 30 degrees and/or prohibiting insertion of tip 470 beyond its pre-movement position. In some examples, the view recentering move may be determined to be invalid when any constraints placed on the movement of imaging device 450 may result in any of the targets no longer being contained in the frustum of view space 350.

In some examples, the view recentering move may be planned as a multi-step move including retracting imaging device 450 away from centroid 440, performing the pitch and/or yaw orientations to align with the viewing direction, and then inserting tip 470 to working distance 480 from centroid 440. In some examples, when the view recentering move includes zooming in, the multi-step move may include performing pitch and/or yaw orientations to align with the viewing direction before inserting tip 470 to working distance 480 from centroid 440. In some examples, when the view recentering move includes zooming out, the multi-step move may include retracting the imaging device to working distance 480 before performing the pitch and/or yaw orientations. In some examples, the multi-step move may help reduce the likelihood that tip 470 collides with the end effectors of articulated arms 310, 320, and/or 330, patient anatomy, and/or other objects in the work space. In some examples, the view recentering move may also include rolling imaging device 450 so that the view up/view coordinate system y-axis aligns with the world coordinate system. In some examples, the view recentering move may be determined using an iterative motion planning operation that optimizes the pitch, yaw, and insertion of imaging device 450 based on accuracy limits in the joints controlling the articulated arm of imaging device 450 so as to minimize orientation and/or positioning errors of imaging device 450.

In some embodiments, when the view recentering move is determined to be invalid, an alternate view recentering move is determined where tip 470 is retracted to a minimum insertion depth. In some examples, the minimum insertion depth may correspond to a depth beyond which the imaging device may become partially occluded by one or more portions of the articulated arm used to position and/or orient imaging device 450. In some examples, the portions of the articulated arm that may partially occlude the imaging device may correspond to cannula 460. In some examples, the minimum insertion depth may correspond to a point a predetermined distance from the remote center for the imaging device. In some examples, the predetermined distance may be based on a length of cannula 460. In some examples, the predetermined distance may be from two to nine centimeters in length. With tip 470 retracted to cannula 460, the viewing direction for imaging device 450 is then set to point toward centroid 440. The maximum x-axis and/or y-axis extent for each of the targets 412-416 and/or 432-434 are then checked to see whether they fall within view space 350. When each of the targets 412-416 and/or 432-434 do not fall within view space 350, the alternate view recentering move is also determined to be invalid. As with the view recentering move, additional checks on the validity of the alternative view recentering move may include determining whether the articulated arm to which imaging device 450 is attached may execute the alternate view recentering move. In some examples, the articulated arm may not be able to execute the alternate view recentering move due to joint limitations, maximum movement limitations placed on view recentering moves, and/or collision avoidance with other articulated arms (e.g., articulated arms 310, 320, and/or 330) and/or patient anatomy. When the alternative view recentering move is invalid, view recentering is aborted and suitable errors are indicated.

Figure 5:
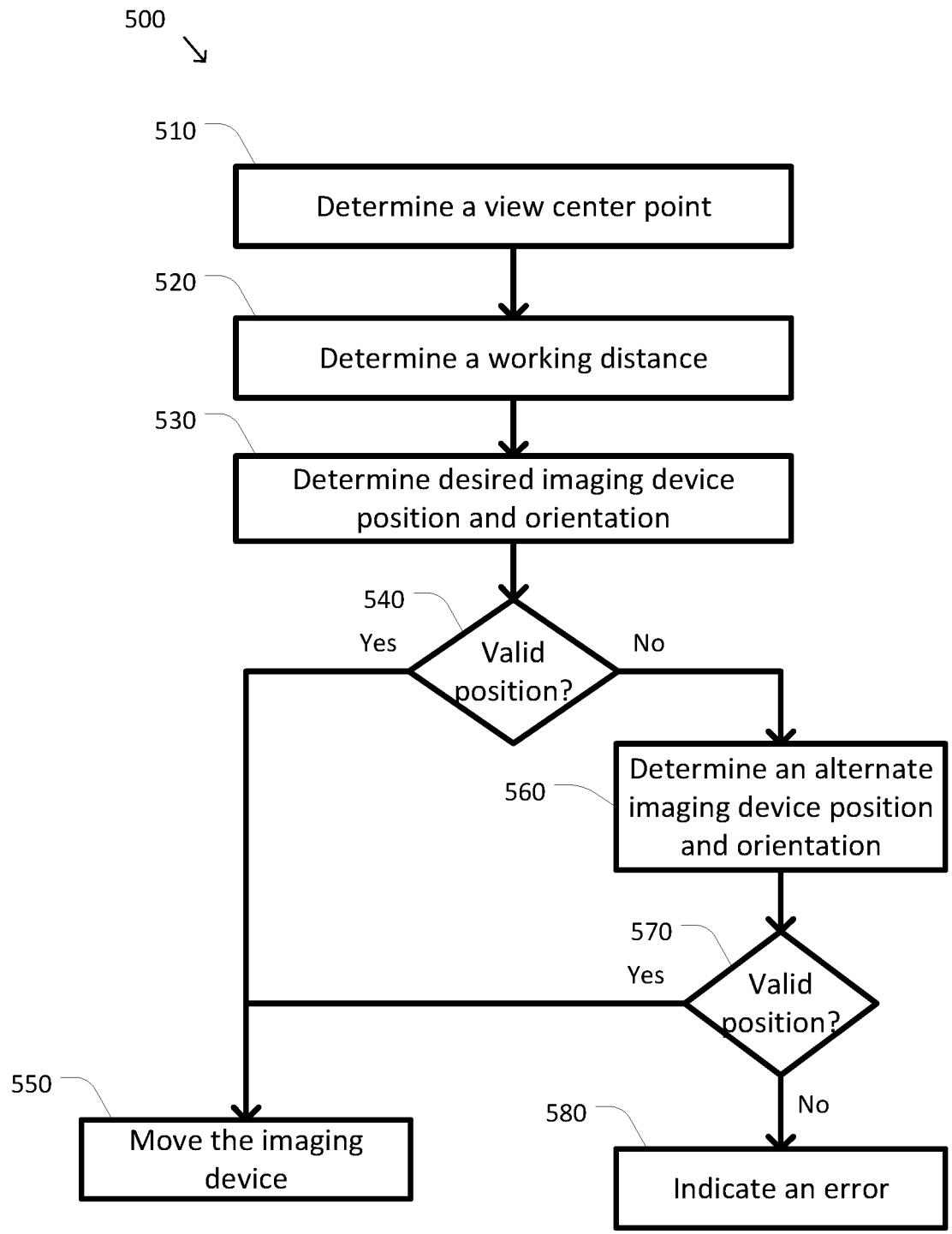
FIG. 5 is a simplified diagram of a method of view recentering according to some embodiments.

FIG. 5 is a simplified diagram of a method 500 of view recentering according to some embodiments. One or more of the processes 510-580 of method 500 may be implemented, at least in part, in the form of executable code stored on non-transient, tangible, machine readable media that when run by one or more processors (e.g., the processor 140 in control unit 130) may cause the one or more processors to perform one or more of the processes 510-580. In some embodiments, method 500 may be performed by an application, such as motion control application 160. In some embodiments, method 500 may be used to recenter one or more of the end effectors 125 and/or the end effectors 310-330 in a view space of an imaging device, such as imaging device 450 so that corresponding images may be displayed on display system 180.

At a process 510, a view center point is determined. In some examples, the view center point may correspond to a centroid of one or more end effectors that are to be recentered in images captured by an imaging device, such as imaging device 450. In the examples of FIGS. 3A, 3B, 4A, and 4B, the end effectors may correspond to the end effectors 310 and 330, and the view center point may correspond to centroid 440. In some examples, the centroid may be determined by taking the centroid of one or more targets, such as targets 412-416 and/or 432-434. In some examples, sensors associated with articulated arms of end effectors 310 and/or 330 may be used to determine positions of joints in the articulated arms. These joint positions in combination with one or more kinematic models of end effectors 310 and/or 330 and their articulated arms may be used to determine the positions of the end effectors 310 and/or 330 that may then be used to determine the centroid.

At a process 520, a working distance is determined. In some examples, the working distance may be determined by determining how far away the targets of the end effectors should be in order for each of the targets to be within a view space of the imaging device. In some examples, the working distance may be determined by determining a maximum x-axis and/or y-axis extent, perpendicular to the direction of view, for each of the targets and then determining respective minimum viewing distances for each of the targets so that the targets are within the frustum of the view space. The largest minimum viewing distance may then be chosen as the working distance so as to ensure that each of the targets is contained in the view space. In some examples, the working distance may be increased to a preferred working distance for the imaging device when one is specified and it is larger than the largest minimum viewing distance. In some examples, the preferred working distance may be set by an operator of the imaging device. In some examples, the working distance may also be constrained to be within minimum and maximum focal distances for the imaging device.

At a process 530, a desired imaging device position and orientation is determined. The orientation of the imaging device by a vector between a reference point on the imaging device and the view center determined during process 510. In some examples, the reference point may correspond to a remote center when the imaging device is straight between the remote center and a tip of the imaging device when the imaging device is constrained by movement about a remote center, such as cannula 460 of imaging device 450. In some examples, one or more kinematic models of the imaging device may be used to determine the location of the reference point. In some examples, the reference point may be associated with the tip of the imaging device. In some examples, the orientation vector may be determined by collocating the tip of the imaging device with the view center while preserving a roll position of the imaging device and then using the view direction of the imaging device as the orientation vector. The position of the tip of the imaging device is then determined based on locating the tip of the imaging device the working distance, as determined during process 520, away from the view center in a direction opposite the direction of view.

At a process 540, it is determined whether the desired imaging device position and orientation is valid. In some examples, this may include determining whether the articulated arm to which the imaging device is attached may execute a view recentering move from its current position and orientation to the imaging device position and orientation determined during process 530. In some examples, the articulated arm may not be able to execute the view recentering move due to joint limitations, maximum movement limitations placed on view recentering moves, and/or collision avoidance with other articulated arms, patient anatomy, and/or other objects in the work space. In some examples, the maximum movement limitations may include pitch and yaw angular limits that limit pitch and yaw motions to 30 degrees or less and/or prohibiting insertion of the imaging device beyond its pre-movement position. In some examples, the view recentering move may be determined to be invalid when any constraints placed on the movement of the imaging device may result in any of the targets no longer being contained in the frustum of the view space. When the desired imaging device position and orientation are valid, the imaging device is moved to the desired imaging device position and orientation using a process 550. When the desired imaging device position and orientation is not valid, an alternate imaging device position and orientation are determined using a process 560.

At the process 550, the imaging device is moved. The imaging device is moved by planning a suitable motion for the imaging device and the articulated arm to which it is attached and then the planned motion is executed by sending one or more commands to the actuators in the articulated arm. In some examples, the motion plan may include a multi-step move including retracting the imaging device away from the view center point, performing pitch and/or yaw orientations to align with the viewing direction so that the imaging device is orientated toward the view center point, and then inserting the imaging device to the working distance from the view center point. In some examples, when the imaging device move includes zooming in, the multi-step move may include performing pitch and/or yaw orientations to align with the viewing direction before inserting the imaging device to the working distance. In some examples, when the imaging device move includes zooming out, the multi-step move may include retracting the imaging device to the working distance before performing the pitch and/or yaw orientations. In some examples, the multi-step move may help reduce the likelihood that the imaging device collides with the end effectors of other articulated arms, patient anatomy, and/or other objects in the work space. In some examples, when the imaging device is to be retracted as determined during process 560, the insertion step may be omitted. In some examples, the planned motion may also include rolling the imaging device so that the view up direction for the imaging device aligns with the world coordinate system. In some examples, one or more kinematic models of the articulated arm associated with the imaging device may be used to aid in the motion planning. In some examples, the planned motion may be determined using an iterative motion planning operation that optimizes the pitch, yaw, and insertion and/or retraction of the imaging device based on accuracy limits in the joints controlling the articulated arm associated with the imaging device so as to minimize orientation and/or positioning errors of the imaging device. Once the imaging device is moved, the recentering operation is completed.

At the process 560, an alternate imaging device position and orientation is determined. When the desired imaging device position and orientation determined during process 540 is invalid, an alternate imaging device position and orientation is determined where the imaging device is retracted away from the view center point. In some examples, the alternate imaging device position and orientation includes retracting the imaging device to a minimum usable insertion depth and ignoring the working distance determined during process 520. In some examples, the minimum insertion depth may correspond to a depth beyond which the imaging device may become partially occluded by one or more portions of the articulated arm used to position and/or orient the imaging device. In some examples, the portions of the articulated arm that may partially occlude the imaging device may correspond to a cannula, such as cannula 460. In some examples, the minimum insertion depth may correspond to a point a predetermined distance from the remote center for the imaging device. In some examples, the predetermined distance may be based on a length of the cannula. In some examples, the predetermined distance may be from two to nine centimeters in length. The alternate imaging device orientation then includes orienting the imaging device toward the view center point using a similar approach as used during process 530.

At a process 570, it is determined whether the alternate imaging device position and orientation is valid. In some examples, this may include determining whether the articulated arm to which the imaging device is attached may execute a view recentering move from its current position and orientation to the alternate imaging device position and orientation determined during process 560. In some examples, the articulated arm may not be able to execute the view recentering move due to joint limitations, maximum movement limitations placed on view recentering moves, and/or collision avoidance with other articulated arms, patient anatomy, and/or other objects in the work space. In some examples, the maximum movement limitations may include pitch and yaw angular limits that limit pitch and yaw motions to 30 degrees or less. When the alternate imaging device position and orientation are valid, the imaging device is moved to the alternate imaging device position and orientation using process 550. When the alternate imaging device position and orientation is not valid, an error is indicated using a process 580.

At the process 580, an error is indicated. When the determined and the alternate imaging device position and orientation are determined to be invalid, the operator is notified. In some examples, the notification may include any suitable audio and/or visual feedback. In some examples, the audio feedback may include playing of a unique sound.

As discussed above and further emphasized here, FIG. 5 is merely an example which should not unduly limit the scope of the claims. One of ordinary skill in the art would recognize many variations, alternatives, and modifications. According to some embodiments, additional conditions and/or safety factors may be considered during method 500 and more particularly during process 550 when the imaging device is under automated movement.

In some embodiments, one or more precautions may be used to reduce and/or prevent contact and/or interference between the imaging device and the anatomy of the patient and/or other obstacles in proximity to the imaging device. In some examples, one or more preoperative and/or intraoperative images of the anatomy of the patient may be used to identify one or more no-fly zones which the imaging device should not enter. In some examples, force and/or torque on one or more of the joints used to manipulate the imaging device may be monitored using suitable sensors to determine whether unexpected forces and/or torques may indicate that the imaging device is in unacceptable contact with the anatomy of the patient and/or other obstacles. In some examples, errors between the commanded positions and/or velocities and actual positions and/or velocities of the imaging device and/or the joints used to manipulate the imaging device may be monitored to determine whether the errors exceed a configurable threshold. In some examples, the configurable threshold may be different for each of the joints. In some examples, the errors may be low-pass filtered and/or smoothed to avoid false positive detections that may be due to otherwise acceptable transient conditions. In some examples, one or more contacts located near the distal end of the imaging device may be monitored to determine whether the imaging device is in contact with the anatomy of the patient and/or other obstacles. In some examples, determination that the imaging device is contacting and/or interfering with the anatomy of the patient may result in premature termination of the movement of the imaging device and/or the activation of one or more visual and/or audio alarms.

In some embodiments, one or more interlocks may be used to ensure that an operator is present to oversee the recentering motion. In some examples, one or more input controls, such as a head-in sensor may be used to determine that an operator is present at an operator console and in position to view images from the imaging device. In some examples, an illumination sensor may be used to determine that images from the imaging device are being displayed to the operator on viewer of the operator console. In some examples, determination that one or more of the interlocks detects absence of the operator and/or loss of images on the imaging device may result in premature termination of the movement of the imaging device and/or the activation of one or more visual and/or audio alarms.

In some embodiments, the motion planned and executed during process 550 may be designed to place an upper limit on velocities and/or accelerations of the imaging device and/or the one or more joints used to manipulate the imaging device. In some examples, the velocities and/or accelerations may be limited so that an operator monitoring the recentering motion may have adequate time to react to potentially undesirable motion in the imaging device and override and/or terminate the recentering motion. In some examples, the velocities and/or accelerations may be limited so that the feed forward torques in the joints used to manipulate the imaging device are kept at sufficiently minimum levels that allow motion in the imaging device that overcomes expected inertia, viscous friction, and/or the like without permitting movement that might result in excessively forceful contact with the anatomy of the patient, other end effectors in proximity to the imaging device, and/or other unexpected obstacles. In some examples, the feedback torques in the joints used to manipulate the imaging device may be limited to minimum values sufficient to overcome expected sources of resistance, such as sterile drapes, friction in a cannula seal, and/or the like.

Figure 6:
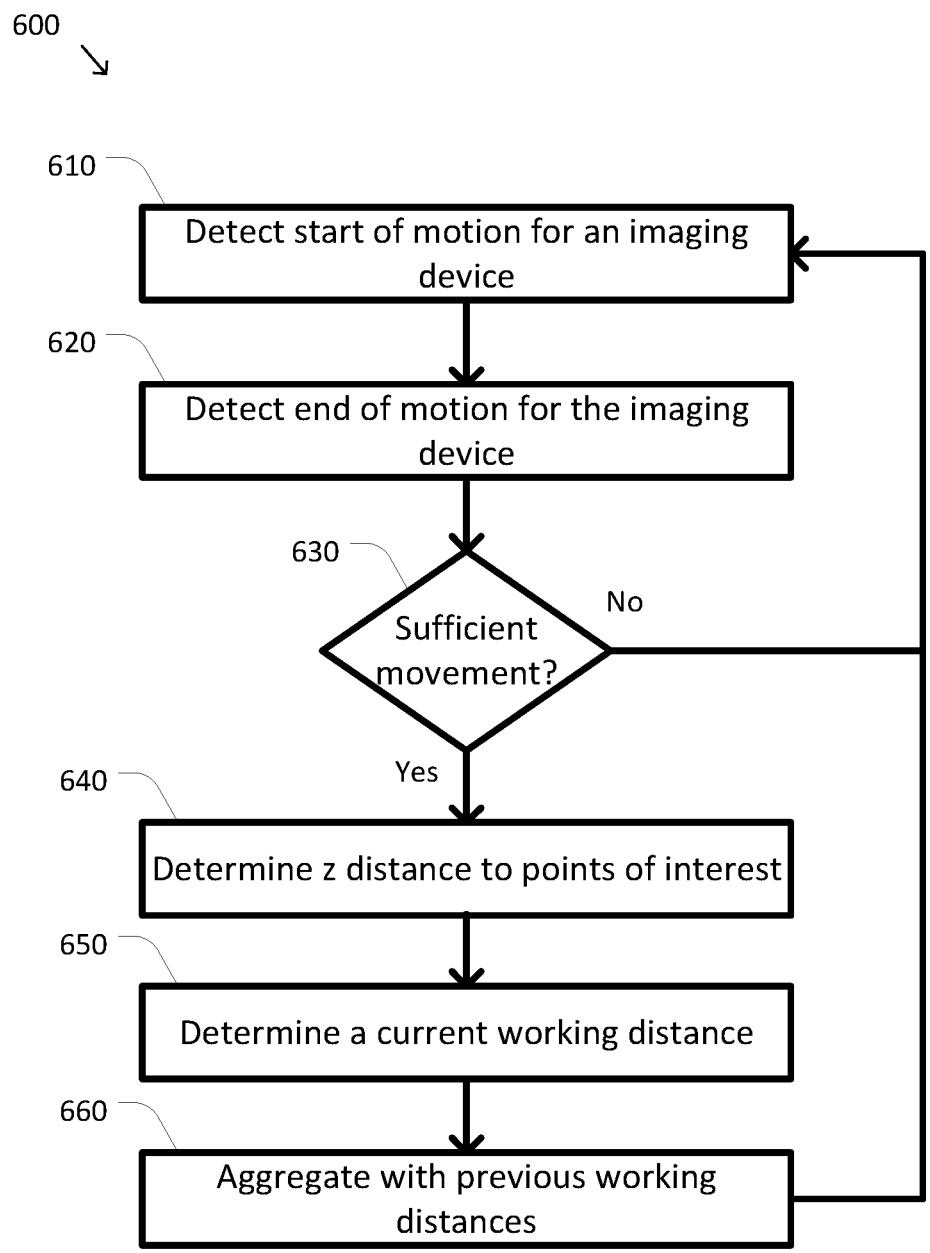
FIG. 6 is a simplified diagram of a method of determining a preferred working distance for an imaging device according to some embodiments.

FIG. 6 is a simplified diagram of a method 600 of determining a preferred working distance for an imaging device according to some embodiments. One or more of the processes 610-660 of method 600 may be implemented, at least in part, in the form of executable code stored on non-transient, tangible, machine readable media that when run by one or more processors (e.g., the processor 140 in control unit 130) may cause the one or more processors to perform one or more of the processes 610-660. In some embodiments, method 600 may be performed by an application, such as motion control application 160. In some embodiments, method 600 may be used to determine the preferred working distance between an imaging device and a view center point. In some examples, the preferred working distance may be the preferred working distance used during process 520. In some embodiments, method 600 may be used to monitor manual repositioning operations of an imaging device by an operator to learn the preferred working distance for the operator.

At a process 610, start of motion for an imaging device is detected. As an operator operates a device with one or more articulated arms and an imaging device, repositioning movements of the imaging device may be monitored. In some examples, the motion of the imaging device may be associated with a tip of the imaging device, such as tip 470. In some examples, the movement of interest may be associated with manual repositioning of the imaging device by the operator. By monitoring the manual repositioning of the imaging device, it is possible to learn the operator's preferred distance between the imaging device and one or more end effectors that are captured in images taken by the imaging device. In some examples, each of the manual repositioning operations may be detected by activation of repositioning and/or reorienting controls for the imaging device. In some examples, when the start of manual repositioning is detected, a current position and/or orientation of the imaging device may be recorded.

At a process 620, end of motion for the imaging device is detected. Once motion of the imaging device is detected during process 610, the motion is monitored until it ends. In some examples, the end of motion may be detected by lack of movement in the imaging device. In some examples, lack of movement may be detected by determining that the velocity of the imaging device falls below a minimum threshold. In some examples, the lack of movement may be detected by determining that the velocity of the imaging device remains below the minimum threshold for a predetermined period of time. In some examples, the end of motion may be associated with the end of the manual repositioning as noted by deactivation of the repositioning and/or reorienting controls. In some examples, when the end of motion is detected, the current position and/or orientation of the imaging device may be recorded.

At a process 630, it is determined whether sufficient motion is detected in the imaging device. Using the current position and/or orientation values recorded during processes 610 and 620, the amount of motion of the imaging device may be determined. In some examples, the amount of motion may be a distance, such as a Euclidean distance, between the starting and ending positions. In some examples, the amount of motion may further be based on the angular changes between the starting and ending orientations. In some examples, the angular changes may be converted to distances by determining a sine and/or a cosine of the angular changes and multiplying one of them by a distance related to a working distance of the imaging device from before the start of motion was detected during process 610. When the amount of motion exceeds a minimum threshold, such as 0.5 cm or so, a new preferred working distance is determined beginning with a process 640. When the amount of motion does not exceed the minimum threshold, method 600 may return to process 610 to detect future motion in the imaging device.

At the process 640, a z distance is determined to points of interest. In some examples, the working distance of the imaging device may be characterized based on the perpendicular distance from the imaging device to one or more points of interest along the direction of view. In some examples, when the points of interests are mapped to a view coordinate system of the imaging device, the z values of each of the points of interest may represent the corresponding z distances. In some examples, the points of interest may correspond to centers of one or more targets on one or more end effectors. In some examples, the end effectors may be chosen by the operator and/or automatically chosen based on the end effectors determined to be visible in images captured by the imaging device. In the examples of FIGS. 4A and 4B, the targets may be selected from the targets 412-416, 422-426, and/or 432-434.

At a process 650, a current working distance is determined. In some examples, the current working distance may be determined by aggregating each of the z distances determined during process 640. In some examples, the aggregation may include an average, a median, a minimum, a maximum, and/or the like. In some examples, a z coordinate of a centroid of the points of interest, such as centroid 440, may be used to determine the current working distance.

At a process 660, the current working distance is aggregated with previous working distances. The current working distance determined during process 650 is aggregated with previous working distance values to determine the preferred working distance. In some examples, the current working distance determined during process 650 may be weighted based on amount of motion between the start and the end of the motion of the imaging device so that larger movements have a greater impact on the preferred working distance. In some examples, the aggregation may include determining a running average, a windowed average over a predetermined period of time, exponential smoothing, and/or the like. In some examples, the preferred working distance may be initialized to a default value. In some examples, the default value may be based on minimum and/or maximum focal lengths for the imaging device. In some examples, the default value may be set to 7 cm or so. In some embodiments, multiple preferred working distances may be determined based on a context of the detected motion. In some examples, the context may include keeping different preferred working distances for different operators, different procedures, different phases of procedures, digital zoom settings, focal distance settings, stereoscopic disparity settings, and/or the like. Once the aggregation is performed, method 600 may repeat to include additional movements in the imaging device in the aggregate that is the preferred working distance.

Figure 7:
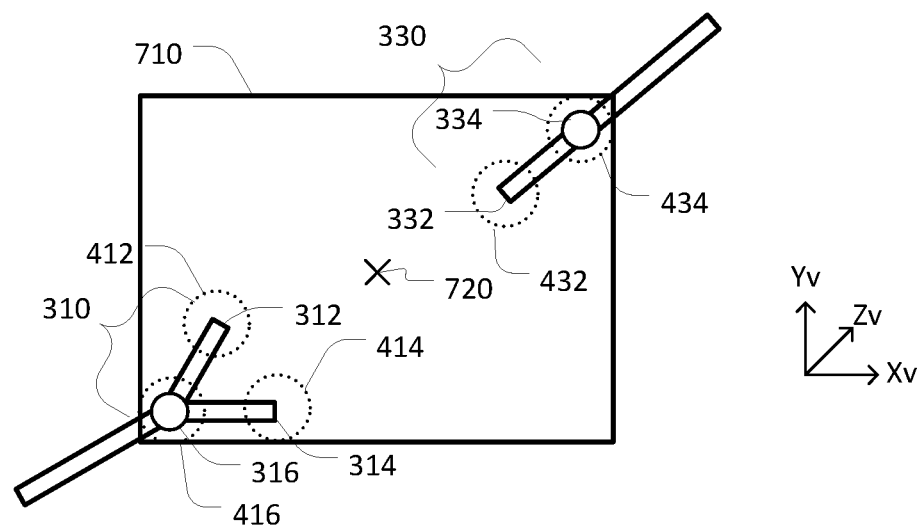
FIG. 7 is a simplified diagram showing a relationship between end effectors in an image on a display system and corresponding input controls in a console workspace following an input control recentering operation according to some embodiments.
Figure 7:
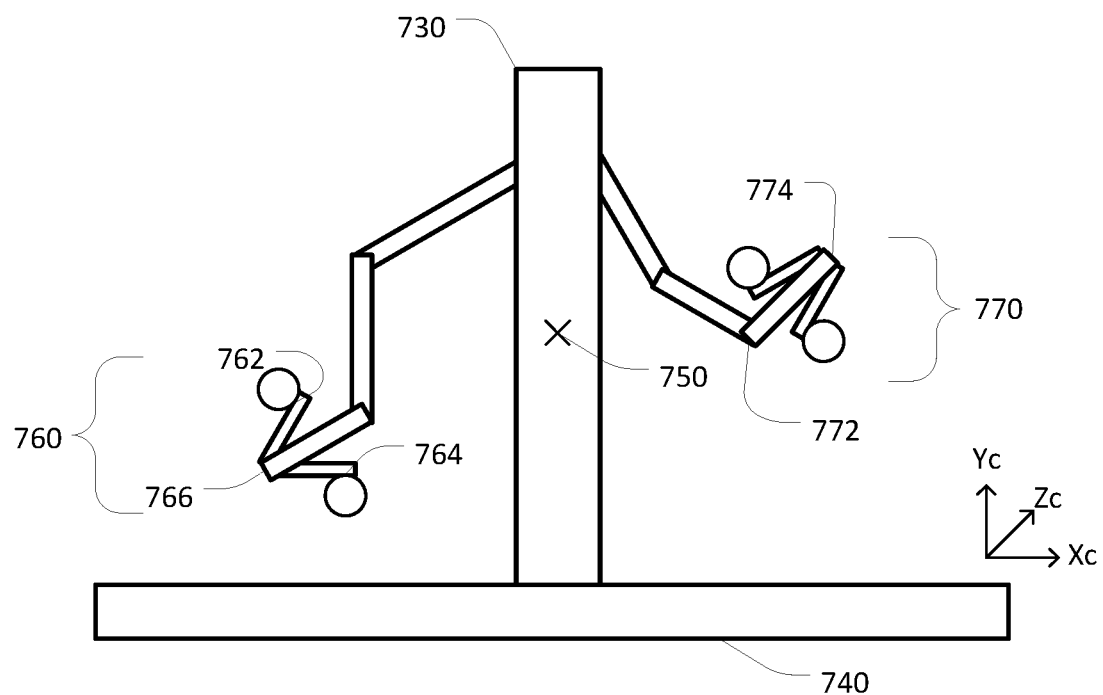

FIG. 7 is a simplified diagram showing a relationship between end effectors in an image on a display system and corresponding input controls in a console workspace following an input control recentering operation according to some embodiments. In some examples, the input control recentering operation may correspond to the input control recentering that occurs as part of the recentering during method 200. In some examples, one of the goals of the recentering operation is to maintain positional and/or orientational harmony between the end effectors, in the view space of an imaging device during the view recentering, and the input controls corresponding to the end effectors. In some examples, the input control recentering includes changing the position and/or orientation of each of the input controls to correspond to the positions and/or orientations of the respective end effectors.

The upper portion of FIG. 7 shows an image of the end effectors 310 and 330 as they may be captured to an image displayed on display system 180 following the view recentering move of FIGS. 3B and 4A. An image captured using imaging device 450 may be displayed on display system 180 as the image shown within borders 710 of display system 180. For purposes of clarity, additional portions of end effectors 310 and 330 and their articulated arms are shown in FIG. 7, even though they would not appear on display system 180 and any objects that may be partially or totally occluding the end effectors are removed from the image as well. A view center point 720 is also shown, which may correspond to centroid 440. In some examples, to facilitate recentering of the input controls, each of the points of interest on the end effectors 310 and 330 may also be mapped to a view coordinate system as depicted by the $x_v$, $y_v$, and $z_v$ axes. In some examples, the points of interest may correspond to the targets 412-416 and/or 432-434.

The lower portion of FIG. 7 shows the console workspace containing input controls 760 and 770 corresponding to the end effectors 310 and 330, respectively. The input controls 760 and 770 may be coupled via their own articulated arms to a body 730 of an operator workstation. In some examples, the console workspace may be positioned relative to an arm rest 740. In some examples, the operator workstation may correspond to operator workstation 170 and arm rest 740 may correspond to arm rest 190. Because each operator may prefer a different height for arm rest 740, have arms, wrists, and/or hands of different sizes and lengths, and/or have different preferences for elbow placement and/or flex, an ergonomic center 750 may be determined within the console workspace. In some examples, a console workspace coordinate system may be defined as shown by the $x_c$, $y_c$, and $z_c$ axes.

In some embodiments, positional and/or orientational harmony between the end effectors 310 and 330 and input controls 760 and 770 may be determined based on mappings between control points on input controls 760 and 770 and corresponding points on the end effectors 310 and 330. More specifically, as shown in the examples, of FIG. 7, control points 762 and 764 on the finger loops of input control 760 may be mapped to the targets 412 and 414, respectively so that as the operator opens and closes the distance between the control points 762 and 764 during teleoperation, the gripping fingers 312 and 314 open and close. Additionally, a control point 766 on input control 760 may be mapped to targeting point 416 so that as pivot point 766 is moved during teleoperation, pivot joint 316 may move correspondingly. Similarly, control points 772 and 774 on input control 770 may be mapped to targets 432 and 434, respectively.

To maintain positional and/or orientational harmony between the end effectors 310 and 330 and the input controls 760 and 770, respectively, the input control recentering operation repositions and/or reorients input controls 760 and 770 about ergonomic center 750 to approximately correspond to the positions and/or orientations of the end effectors 310 and 330 within the view space corresponding to the image with borders 710. Thus, as shown in FIG. 7, input control 760 is positioned to a lower-left portion of the console workspace and is oriented in an upward and right direction that matches the position and orientation of the end effector 310. Similarly, input control 770 is positioned in an upper-right portion of the console workspace and is oriented in a downward and left direction that matches the position and orientation of the end effector 330. To maintain the positional and/or orientational harmony, the view and console stereoscopic viewer workspace coordinate system are typically aligned in the left-right ($x_c$ and $x_v$), up-down ($y_c$ and $y_v$), and in-out ($z_c$ and $z_v$) directions. In general, this provides for intuitive operation of the end effectors 310 and/or 330 during teleoperation as operator hand movements of the input controls may be translated to corresponding movements of the end effectors 310 and/or 330.

In some embodiments, positional and/or orientational harmony between the end effectors 310 and 330 and the input controls 760 and 770, respectively, may be maintained by mapping the targets 412-416 and/or 432-434 of the end effectors 310 and 330 from the view coordinate system to the console workspace coordinate system and then using one or more actuators in the articulated arms associated with the input controls 760 and 770 to position and/or orient the corresponding control points 762-766 and/or 772-774 at the mapped locations in the console workspace coordinate system. In some examples, this may be accomplished using translating and scaling transformations. In some examples, one or more translation transformations may be used to map view center point 720 to ergonomic center 740. Once the view center point 720 and the ergonomic center 740 are aligned, distances in the view coordinate system may be scaled to corresponding distances in the console workstation coordinate system. In some examples, one or more scale factors for the scaling may be set by the operator of the operator workstation. In some examples, the one or more scale factors may be set based on the relative sizes of image border 710 and the console workspace. Once each of the points 312-316 and/or 332-334 of the end effectors are mapped to determine the positions of the corresponding control points 762-766 and/or 772-774, a motion plan for the input controls 760 and 770 may be developed and performed.

In some embodiments, the positions of each of the control points 762-766 and/or 772-774 may be constrained before the motion plan is developed and performed. In some examples, the position and/or orientation of the control points 762-766 and/or 772-774 may be constrained by range of motion limits of joints in the corresponding articulated arms, to maintain a minimum and/or a maximum distance between input controls 760 and 770, to avoid collisions with arm rest 740 and/or other portions of the operator workstation, to prevent a left/right crisscrossing of input controls 760 and 770, to avoid undesirable positions and/or orientations of input controls 760 and 770, to account for positional accuracy of the targets 412-416 and/or 432-434 and/or the control points 762-766 and/or 772-774 (e.g., 1 cm or so), and/or the like.

Although not shown in FIG. 7, the front to back positioning of the input controls 760 and/or 770 are matched to the depth of the corresponding end effectors 310 and/or 330. Thus the $z_v$ coordinates of the targets 412-416 and/or 432-434 are correspondingly shifted and scaled to determine the $z_c$ coordinates of the control points 762-766 and/or 772-774. Thus, consistent with the side view relationship shown in FIG. 4B, control points 672 and 674 may be located closer to the operator than control points 762-766.

Figure 8:
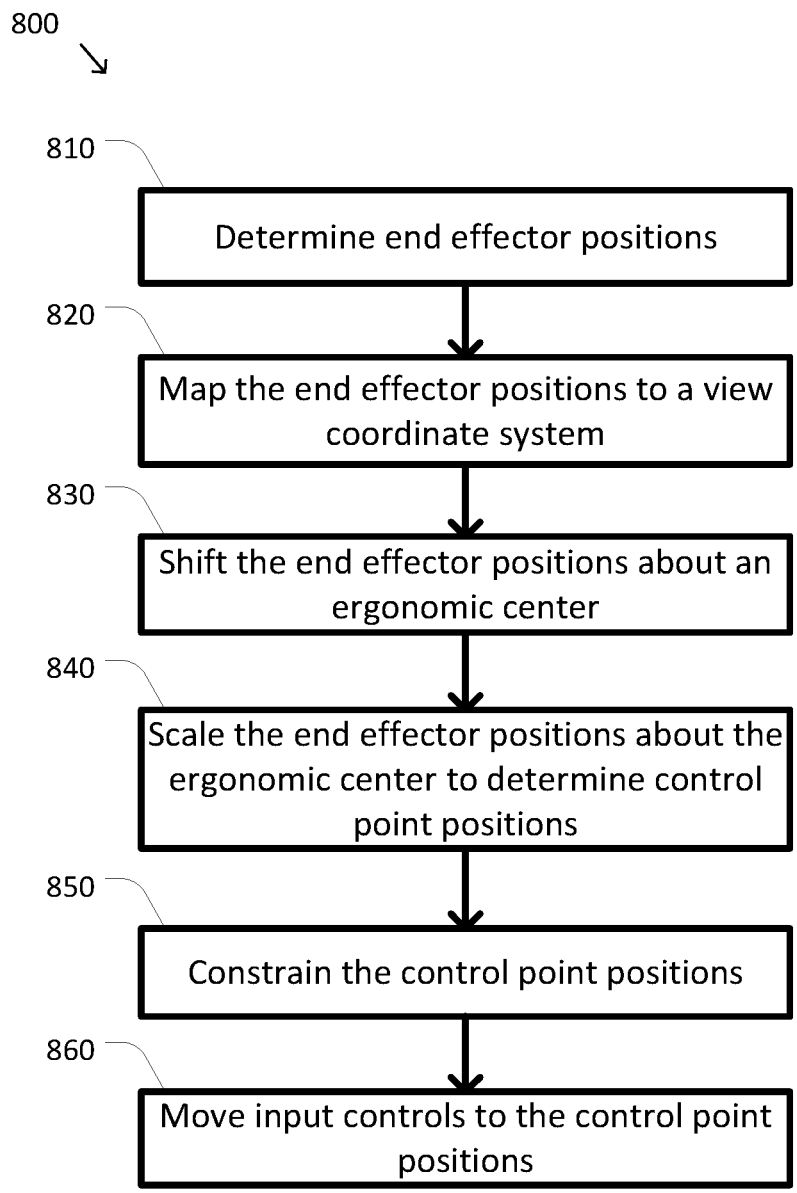
FIG. 8 is a simplified diagram of a method of input control recentering according to some embodiments.

FIG. 8 is a simplified diagram of a method 800 of input control recentering according to some embodiments. One or more of the processes 810-860 of method 800 may be implemented, at least in part, in the form of executable code stored on non-transient, tangible, machine readable media that when run by one or more processors (e.g., the processor 140 in control unit 130) may cause the one or more processors to perform one or more of the processes 810-860. In some embodiments, method 800 may be performed by an application, such as motion control application 160. In some embodiments, method 800 may be used to recenter one or more of the input controls 195, 760, and/or 770 in a console workspace to maintain positional and/or orientational harmony with corresponding end effectors 125, 310, 320, and/or 330 as displayed in an image captured by an imaging device, such as imaging device 450, and displayed on display system 180.

At a process 810, end effector positions are determined. In some examples, sensors associated with articulated arms associated with the end effectors may be used to determine positions of joints in the articulated arms. These joint positions in combination with one or more kinematic models of the articulated arms and the end effectors may be used to determine the positions of the end effectors. In some examples, one or more images of the end effectors may be used to determine the positions of the end effectors. In the examples of FIGS. 3A, 3B, 4A, 4B, and 7 the end effectors may correspond to the end effectors 310 and 330, with the positions of the end effectors 310 and/or 330 being characterized by the targets 412-416 and/or 432-434.

At a process 820, the end effector positions are mapped to a view coordinate system. Using sensors associated with an articulated arm associated with an imaging device and one or more kinematic models of the articulated arm associated with the imaging device, a view coordinate system is determined for the imaging device. The end effector positions determined during process 810 are then mapped to the view coordinate system. This mapping helps determine the x and y positions of the end effectors in images captured by the imaging device as well as z positions of the end effectors that indicate how far the end effectors are from the imaging device in the direction of view. In the examples, of FIG. 7, the end effector positions in the view coordinate system may correspond to the $x_v$, $y_v$, and $z_v$ coordinate values of the targets 412-416 and/or 432-434.

At a process 830, the end effector positions are shifted about an ergonomic center. To help maintain positional and/or orientational harmony between the end effectors and one or more input controls of an operator console, the view coordinate system is mapped to a console workspace coordinate system. In some examples, the mapping between the view coordinate system and the console workspace coordinate system begins by associating a center point in the view coordinate system with a center point in the console workspace coordinate system. In some examples, a centroid of the end effector positions may be selected as the center point in the view coordinate system. In some examples, the ergonomic center of the console workspace may be selected as the center point of the console workspace coordinate system. In some examples, the two center points may be associated by using one or more translation transformations when the origins of the view coordinate system and/or the console workspace coordinate system do not coincide with the selected center points. In some examples, the ergonomic center of the console workspace may be preselected by an operator of the operator console and/or by the geometry of the operator console and its input controls. In some examples, the ergonomic center may be moved when one or more rests, such as an arm rest on the console workstation is repositioned. In some examples, the ergonomic center may be learned by monitoring operation of the operator workstation as is discussed in further detail with respect to FIG. 9. In the examples, of FIG. 7, process 830 corresponds to aligning centroid 720 with ergonomic center 750.

At a process 840, the end effector positions are scaled about the ergonomic center to determine control point positions. Because the scales of the view coordinate system and the console workspace coordinate system typically differ, the positions of the end effectors in the view coordinate system relative to the center point in the view coordinate system are scaled about the ergonomic center in the console workspace coordinate system. The scaling converts relative distances between the end effector positions and the center point in the view coordinate system into corresponding relative distances between the input control positions and the ergonomic center in the console workspace coordinate system. Each of the scaled points from the view coordinate system then becomes a control point in the console workspace coordinate system. In some examples, one or more scale factors for the scaling may be set by the operator of the operator workstation. In some examples, the one or more scale factors may be set based on the relative sizes of images captured in the view coordinate system and the size of the console workspace. In the examples, of FIG. 7, the scaling of process 840 converts relative $x_v$, $y_v$, and $z_v$ distances to $x_c$, $y_c$, and $z_c$ distances, respectively, so that positions of the targets 412-416 and/or 432-434 are converted to positions of the control points 762-766 and/or 772-774, respectively.

At a process 850, the control point positions are constrained. In some examples, the mapping of points associated with the end effector positions in the view coordinate system to the control point positions in the console workspace coordinate system may not result in suitable positions and/or orientations for input controls, such as input controls 195, 760, and/or 770. In some embodiments, the positions of each of the control points mapped during processes 830 and/or 940 may be constrained. In some examples, the position and/or orientation of the control points may be constrained by range of motion limits of joints in corresponding articulated arms, to maintain a minimum and/or a maximum distance between control points of different input controls, to avoid collisions with an arm rest and/or other portions of the operator workstation, to prevent a left/right crisscrossing of the input controls, to avoid undesirable positions and/or orientations of the input controls, to account for limits in positional accuracy of either the points of the end effectors and/or the control points of the input controls (e.g., 1 cm or so), and/or the like.

At a process 860, the input controls are moved to the control point positions. Using one or more kinematic models of the articulated arms associated with the input controls, a motion plan is determined from the input controls that moves the control points on the input controls from their previous positions to the control point positions determined using processes 830-850. In some examples, when the desired motions of the input controls and the control point positions may result in collisions and/or near collisions between the articulated arms associated with the input controls, the motion plan may include multiple segment plans with intermediate control position points that avoid the collisions and/or near collisions. The motion plan may then be implemented by sending one or more commands to actuators associated with the articulated arms. In some examples, when no suitable motion plan may be determined, an error is indicated.

Figure 9:
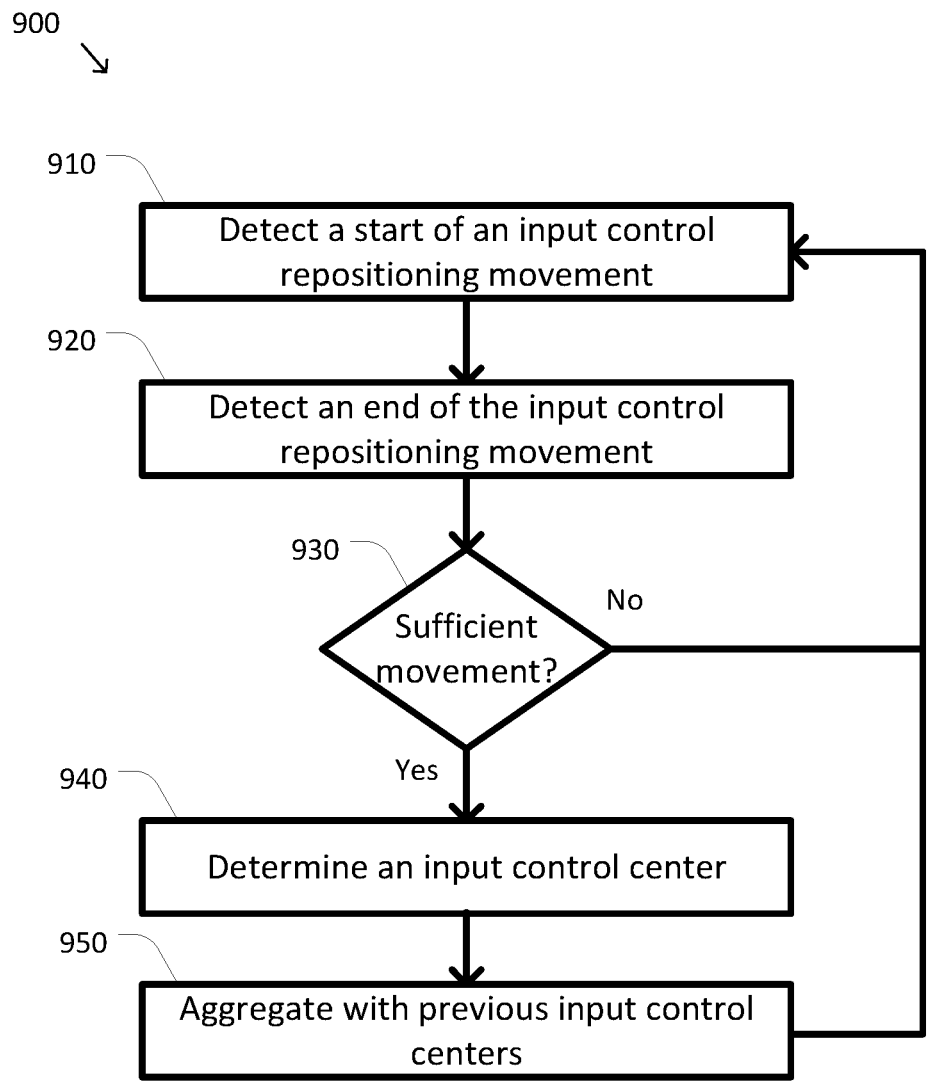
FIG. 9 is a simplified diagram of a method of determining an ergonomic center for input controls according to some embodiments.

FIG. 9 is a simplified diagram of a method 900 of determining an ergonomic center for input controls according to some embodiments. One or more of the processes 910-950 of method 900 may be implemented, at least in part, in the form of executable code stored on non-transient, tangible, machine readable media that when run by one or more processors (e.g., the processor 140 in control unit 130) may cause the one or more processors to perform one or more of the processes 910-950. In some embodiments, method 900 may be performed by an application, such as motion control application 160. In some embodiments, method 900 may be used to determine the ergonomic center of one or more input controls in a console workspace. In some embodiments, method 900 may be used to monitor manual repositioning operations of the input controls to learn the preferred ergonomic center for an operator.

At a process 910, start of an input control repositioning movement is detected. During the operation of a teleoperated device using an operator workstation, the operator may periodically reposition one or more input controls into a more comfortable and/or ergonomic position. In some examples, this may be triggered by the operator engaging a clutch that disengages movements of the input controls from the end effectors being teleoperated by the respective input controls. In some examples, detecting engagement of the clutch indicates the start of an input control repositioning movement. In some examples, when the start of the input control repositioning movement is detected, a current position and/or orientation of the input controls may be recorded for one or more control points of the input controls.

At a process 920, end of the input control repositioning movement is detected. When the operator completes the input control repositioning movement, the clutch is disengaged and teleoperation of the articulated arms and end effectors is resumed. In some examples, detecting disengagement of the clutch indicates the end of the input control repositioning movement. In some examples, when the end of the input control repositioning movement is detected, a current position and/or orientation of the input controls may be recorded based on the one or more control points of the input controls.

At a process 930, it is determined whether sufficient motion is detected in the input controls between the start and the end of the input control repositioning movement. Using the current position and/or orientation values recorded during processes 910 and 920, the amount of motion of the input controls may be determined. In some examples, the amount of motion may be a distance, such as a Euclidean distance, between the starting and ending positions. In some examples, the amount of motion may be an aggregation of one or distances between starting and ending positions of the one or more control points. In some examples, the aggregation may be a sum, a weighted sum, an average, and/or the like. When the amount of motion exceeds a minimum threshold, such as 2 cm or so, an input control center is determined beginning with a process 940. When the amount of motion does not exceed the minimum threshold, method 900 may return to process 910 to detect future input control repositioning movements.

At the process 940, an input control center is determined. Using the ending positions of the input controls recorded during process 920, the center of the input controls is determined. In some examples, the center of the input controls may be determined using an aggregation, such as a centroid, of the ending positions of the one or more control points of the input controls.

At a process 950, the input control center is aggregated with previous input control centers. The input control center determined during process 940 is aggregated with previous input control centers to determine the ergonomic center. In some examples, the input control center determined during process 940 may be weighted based on amount of motion between the start and the end of the input control repositioning movement so that larger movements have a greater impact on the ergonomic center. In some examples, the aggregation may include determining a running average, a windowed average over a predetermined period of time, exponential smoothing, and/or the like. In some examples, the ergonomic center may be initialized to a default value. In some examples, the default value may be based on geometries of the input controls, the console workspace, and/or anticipated physiology of the operator. In some embodiments, multiple ergonomic centers may be determined based on a context of the detected motion. In some examples, the context may include keeping different ergonomic centers for different operators, different procedures, different phases of procedures, different end effectors being teleoperated by the input controls, and/or the like. Once the aggregation is performed, method 900 may repeat to include additional input control repositioning movements in the aggregate that is the ergonomic center. In some examples, the ergonomic center may be adjusted to account for a position of one or more rests, such as an arm rest, in the console workspace.

Figure 10:
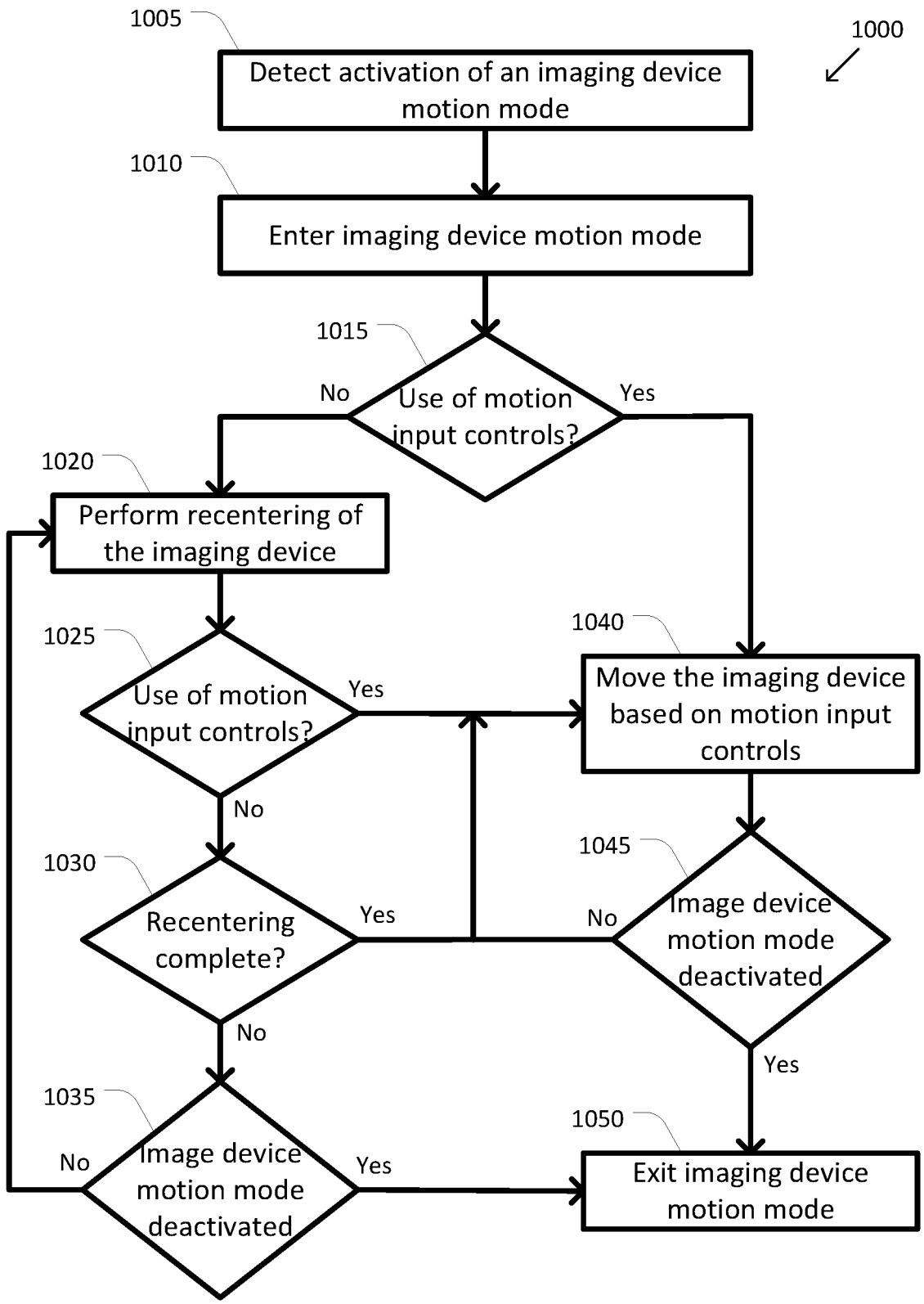
FIG. 10 is a simplified diagram of a method of controlling an imaging device according to some embodiments.

FIG. 10 is a simplified diagram of a method 1000 of controlling an imaging device according to some embodiments. One or more of the processes 1005-1050 of method 1000 may be implemented, at least in part, in the form of executable code stored on non-transient, tangible, machine readable media that when run by one or more processors (e.g., the processor 140 in control unit 130) may cause the one or more processors to perform one or more of the processes 1005-1050. In some embodiments, method 1000 may be performed by an application, such as motion control application 160. In some embodiments, method 1000 may be used to combine manual control of an imaging device, such as imaging device 450, using one or more input controls in a console workspace with automated recentering of the imaging device. In some embodiments, variations in the processes are possible. In some examples, processes 1020-1035 may be performed in different orders and/or substantially in parallel.

At a process 1005, activation of an imaging device motion mode is detected. In some examples, an operator of an electronic device may manually trigger the activation of the imaging device motion mode using one or more input controls such as a switch, a button, a pedal, a level, voice recognition, and/or the like. In some example, the request may be issued as a momentary input which triggers imaging device motion mode and/or as a continuous input which activates the imaging device motion mode.

At a process 1010, imaging device motion mode is entered. In some examples, before imaging device motion mode is entered, operator control of one or more end effectors is suspended. In some examples, one or more motion input controls, such as one or more of the master controls 195 may be decoupled from control of the one or more end effectors. In some examples, the decoupling may occur due to a limited number of operator controls for controlling devices attached to the distal end of articulated arms and/or to limit the ability of the operator to control and/or teleoperate one or more of the end effectors of the electronic device. Suspension of control by the operator permits the imaging device to be moved without interference from motions of the one or more end effectors commanded by the operator.

At a process 1015, it is determined whether one or more of the motion input controls is being used. In some examples, upon entering the imaging device motion mode during process 1010, a timeout period may begin. During the timeout period the one or more motion input controls may be monitored to determine whether the operator is attempting to manually control the position and/or orientation of the imaging device using the one or more motion input controls. In some examples, the timeout period may be of a configurable length, such as 0.5 seconds or so. In some examples, use of the one or more motion input controls may be determined based on whether the operator moves one or more of the motion input controls more than a threshold distance, rotates one or more of the motion input controls through more than a threshold angle, and/or some aggregate combination of both. In some examples, the threshold distance may be 5-10 mm. In some examples, the threshold angle may be 5 degrees or higher. When the timeout period ends with no use of the one or more motion input controls, recentering begins starting with a process 1020. When use of the one or more input controls is detected during the timeout period, manual control of the imaging device begins with a process 1040.

At the process 1020, recentering of the imaging device is performed. In some examples, processes similar to processes 510-580 of method 500 may be used to perform the recentering of the imaging device during process 1020. In some examples, while the imaging device is being recentered during process 1020, the one or more motion input controls may be automatically moved to maintain positional and/or orientational harmony between the one or more motion input controls and the imaging device. In some examples, processes similar to processes 810-860 of method 800 may be modified to maintain the positional and/or orientational harmony between the one or more motion input controls and the imaging device with the position and/or orientation of the imaging device being substituted for the position and/or orientation of the end effectors.

At a process 1025, it is determined whether one or more of the motion input controls is being used. In some examples, use of the one or more motion input controls may correspond to deliberate motion of the one or more motion input controls by the operator and/or sufficient resistance by the operator to changes in the position and/or orientation of the one or more motion input controls as the positional and/or orientational harmony between the one or more motion input controls and the imaging device is being maintained. In some examples, deliberate motion may be detected using an approach similar to the approach used during process 1015. In some examples, resistance by the operator may be detected by determining a difference between a commanded and an actual position and/or orientation of the motion input controls that exceed a threshold distance and/or a threshold angle. In some examples, the threshold distance may be 1 to 3 cm or so. In some examples, the threshold angle may be 5 degrees or higher. When no use of the one or more motion input controls is detected, recentering continues with a process 1030. When use of the one or more input controls is detected, manual control of the imaging device begins with the process 1040.

At the process 1030, it is determined whether the recentering is complete. The recentering being performed by process 1020 is monitored to determine whether the motion planned as part of the recentering is complete with the imaging device having the desired pose. When the recentering is complete, manual control of the imaging device begins with the process 1040. When the recentering is not complete, recentering continues with a process 1035.

At the process 1035, it is determined whether deactivation of the imaging device motion mode is detected. In some examples, the operator may indicate deactivation of the imaging device motion mode using one or more input controls such as a switch, a button, a pedal, a level, voice recognition, and/or the like. In some example, when the request to activate the imaging device motion mode was activated during process 1005 using a momentary input, a complementary momentary input may be used to deactivate the imaging device motion mode. In some examples, when the request to activate the imaging device motion mode was activated during process 1005 using a continuous input, removal of the continuous input, such as removing a foot from a pedal, may be used to deactivate the imaging device motion mode. In some examples, one or more of the precautions, safety features, and/or interlocks associated with method 500 and/or process 550 may be used to determine that deactivation of the imaging device motion mode should occur. When deactivation of the imaging device motion mode is not detected, recentering continues by repeating processes 1020-1035. When deactivation of the image device motion mode is detected, imaging device motion mode is exited using a process 1050.

At the process 1040, the imaging device is moved based on the motion input controls. In some examples, the motion input controls may be used to manually control the position and/or orientation of the imaging device. In some examples, the imaging device may be moved to maintain the positional and/or orientational harmony between the one or more motion input controls and the imaging device. In some examples, the motion input controls may be used to teleoperate the imaging device by mirroring changes in the positions and/or orientations of the motion input controls to corresponding changes in the position and/or orientation of the imaging device. In some examples, one or more kinematic models of the motion input controls, the imaging device, and/or the articulated arm to which the imaging device is attached may be used to convert the changes in the motion input controls to the corresponding changes in the imaging device. In some examples, the one or more kinematic models may be used to determine one or more coordinate transformation matrices that map the changes in the motion input controls to the corresponding changes in the imaging device. In some examples, the coordinate transformation matrices may implement one or more shift and/or scale transformations. In some examples, the changes in the position and/or orientation of the imaging device may be executed by sending one or more commands to the actuators in the articulated arm to which the imaging device is attached.

At a process 1045, it is determined whether deactivation of the imaging device motion mode is detected. Using a process similar to process 1035 it is determined whether the imaging device motion mode is to be exited. When deactivation of the imaging device motion mode is not detected, manual control of the imaging device continues by repeating process 1040. When deactivation of the image device motion mode is detected, imaging device motion mode is exited using the process 1050.

At the process 1050, the imaging device motion mode is exited. Upon deactivation of the imaging device motion mode during processes 1035 and/or 1045, the imaging device motion mode is exited. In some examples, upon exiting of the imaging device motion mode any motion of the imaging device due to the recentering of process 1020 is ended and the one or more motion input controls are decoupled from controlling the position and/or orientation of the imaging device. In some examples, upon exiting the imaging device motion mode, manual and/or recentering control of the imaging device ends. In some examples, upon exiting the imaging device motion mode, the electronic device may be returned to a mode where the one or more motion input controls become dormant and/or revert to control of one or more end effectors of the electronic device.

Some examples of control units, such as control unit 130 may include non-transient, tangible, machine readable media that include executable code that when run by one or more processors (e.g., processor 140) may cause the one or more processors to perform the processes of methods 200, 500, 600, 800, 900, and/or 1000. Some common forms of machine readable media that may include the processes of methods 200, 500, 600, 800, 900, and/or 1000 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/ or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
an input control for teleoperating an end effector, wherein during teleoperation, movement of the input control by an operator is to command corresponding movement of the end effector; and
a control unit comprising one or more processors coupled to the end effector and the input control;
wherein the control unit is configured to:
suspend teleoperated control of the end effector by the input control in response to a recentering request;

determine an input control recentering move to provide positional and orientational harmony between the input control and the end effector;

execute the input control recentering move to move the input control; and reinstate teleoperated control of the end effector by the input control.

2. The computer-assisted device of claim 1, wherein to determine the input control recentering move, the control unit is configured to:

determine one or more first positions associated with the end effector;

map the one or more first positions to a view coordinate system;

map the one or more first positions from the view coordinate system to a console workspace coordinate system; and determine one or more second positions for one or more control points on the input control, the one or more control points corresponding to the mapped one or more first positions in the console workspace coordinate system.

3. The computer-assisted device of claim 2, wherein the one or more first positions correspond to one or more targets associated with the end effector.

4. The computer-assisted device of claim 2, wherein the view coordinate system is determined relative to an imaging device.

5. The computer-assisted device of claim 2, wherein to map the one or more first positions from the view coordinate system to the console workspace coordinate system, the control unit is configured to scale the one or more first positions relative to an ergonomic center based on one or more distances, the one or more distances being between a view center point and the one or more first positions in the view coordinate system.

6. The computer-assisted device of claim 5, wherein to map the one or more first positions from the view coordinate system to the console workspace coordinate system, the control unit is further configured to translate the view center point in the view coordinate system to the ergonomic center in the console workspace coordinate system.

7. The computer-assisted device of claim 5, wherein to determine the ergonomic center, the control unit is configured to:

detect a start of a repositioning movement for the input control;

detect an end of the repositioning movement;

determine third positions of the one or more control points at the end of the repositioning movement;

aggregate the third positions to determine an input control center point; and aggregate the input control center point with previously obtained input control center points to determine the ergonomic center.

8. The computer-assisted device of claim 7, wherein to aggregate the third positions, the control unit is configured to determine a centroid of the third positions.

9. The computer-assisted device of claim 7, wherein the control unit is further configured to determine whether sufficient motion of the input control occurs between the start and the end of the repositioning movement.

10. The computer-assisted device of claim 7, wherein the control unit is further configured to weight the input control center point based on an amount of motion of the input control between the start and the end of the repositioning movement.

11. A method comprising:

suspending, by one or more processors, teleoperated control of an end effector by an input control of a computer-assisted device in response to a recentering request, wherein during the teleoperated control, movement of the input control by an operator is to command a corresponding movement of the end effector;

determining, by the one or more processors, an input control recentering move to provide positional and orientational harmony between the input control and the end effector;

executing, by the one or more processors, the input control recentering move to move the input control; and reinstating, by the one or more processors, teleoperated control of the end effector by the input control.

12. The method of claim 11, wherein determining the input control recentering move comprises:

determining one or more first positions associated with the end effector;

mapping the one or more first positions to a view coordinate system;

mapping the one or more first positions from the view coordinate system to a console workspace coordinate system; and determining one or more second positions for one or more control points on the input control, the one or more control points corresponding to the mapped one or more first positions in the console workspace coordinate system.

13. The method of claim 12, wherein the one or more first positions correspond to one or more targets associated with the end effector.

14. The method of claim 12, wherein mapping the one or more first positions from the view coordinate system to the console workspace coordinate system comprises scaling the one or more first positions relative to an ergonomic center based on one or more distances, the one or more distances being between a view center point and the one or more first positions in the view coordinate system.

15. The method of claim 14, further comprising:

detecting a start of a repositioning movement for the input control;

detecting an end of the repositioning movement;

determining third positions of the one or more control points at the end of the repositioning movement;

aggregating the third positions to determine an input control center point; and aggregating the input control center point with previously obtained input control center points to determine the ergonomic center.

16. One or more non-transitory machine-readable media comprising a plurality of machine readable instructions that, when executed by one or more processors associated with a computer-assisted device, are adapted to cause the one or more processors to perform a method comprising:

suspending teleoperated control of an end effector by an input control of the computer-assisted device in response to a recentering request, wherein during the teleoperated control, movement of the input control by an operator is to command corresponding movement of the end effector;

determining an input control recentering move to provide positional and orientational harmony between the input control and the end effector;

executing the input control recentering move to move the input control; and reinstating teleoperated control of the end effector by the input control.

17. The one or more non-transitory machine-readable media of claim 16, wherein determining the input control recentering move comprises:
  determining one or more first positions associated with the end effector;
  mapping the one or more first positions to a view coordinate system;
  mapping the one or more first positions from the view coordinate system to a console workspace coordinate system; and
  determining one or more second positions for one or more control points on the input control, the one or more control points corresponding to the mapped one or more first positions in the console workspace coordinate system.

18. The one or more non-transitory machine-readable media of claim 17, wherein the one or more first positions correspond to one or more targets associated with the end effector.

19. The one or more non-transitory machine-readable media of claim 17, wherein mapping the one or more first positions from the view coordinate system to the console workspace coordinate system comprises scaling the one or more first positions relative to an ergonomic center based on one or more distances, the one or more distances being between a view center point and the one or more first positions in the view coordinate system.

20. The one or more non-transitory machine-readable media of claim 19, wherein the method further comprises:
  detecting a start of a repositioning movement for the input control;
  detecting an end of the repositioning movement;
  determining third positions of the one or more control points at the end of the repositioning movement;
  aggregating the third positions to determine an input control center point; and
  aggregating the input control center point with previously obtained input control center points to determine the ergonomic center.

* * * * *

UNITED STATES PATENT AND TRADEMARK OFFICE
CERTIFICATE OF CORRECTION

PATENT NO. : 11,246,671 B2
APPLICATION NO. : 16/503403
DATED : February 15, 2022
INVENTOR(S) : Brandon D. Itkowitz et al.

It is certified that error appears in the above-identified patent and that said Letters Patent is hereby corrected as shown below:

On the Title Page

Column 1, Line 1:
(63) Related U.S. Application Data:
Please delete "Continuation of application No. 15/125,679, filed as application No. PCT/US2015/021105 on Mar. 17, 2015, now Pat. No. 10,398,521." and insert --Continuation of application No. 15/125,679, filed on Sep. 13, 2016, now Pat. No. 10,398,521, which is a 371 of application No. PCT/US2015/021105, filed on Mar. 17, 2015.--;

On page 2, Other Publications Column 2, Line 5:
(56) References Cited:
Please delete "Bajdt et al., "Robotics" In: "Robotics", Jan. 15, 2010 (Jan. 15, 2010), Springer Netherlands, Dordrecht, XP055384691, ISBN: 978-90-48-13776-3, 1 page." and insert --Bajd T. et al., "Robotics" In: "Robotics", Jan. 15, 2010 (Jan. 15, 2010), Springer Netherlands, Dordrecht, XP055384691, ISBN: 978-90-48-13776-3, 1 page.--.

Signed and Sealed this
Twenty-fifth Day of April, 2023

Katherine Kelly Vidal
*Director of the United States Patent and Trademark Office*